United States Patent [19]

Catt et al.

[11] Patent Number: 5,011,947
[45] Date of Patent: Apr. 30, 1991

[54] ANTIHYPERCHOLESTEROLEMIC ALKYLENE COMPOUNDS

[75] Inventors: John D. Catt, Southington; John J. Wright, Guilford, both of Conn.

[73] Assignee: Bristol-Myers, New York, N.Y.

[21] Appl. No.: 538,583

[22] Filed: Jun. 12, 1990

Related U.S. Application Data

[63] Continuation of Ser. No. 236,579, Aug. 25, 1988, abandoned.

[51] Int. Cl.$^5$ .................... C07D 301/36; C09F 7/08
[52] U.S. Cl. .................................. 549/292; 260/405.5
[58] Field of Search ....................... 260/405.5; 549/292

[56] References Cited

FOREIGN PATENT DOCUMENTS 18881 8/1988 Australia .
312269 4/1989 European Pat. Off. .

OTHER PUBLICATIONS

Tetrahedron Letters, vol. 29, No. 8, 929–930 (1988).

*Primary Examiner*—Anton H. Sutto
*Attorney, Agent, or Firm*—Aldo A. Algieri; William T. Han

[57] ABSTRACT

Compounds of the formula

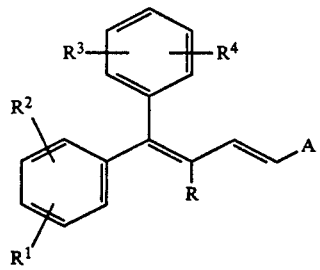

I wherein
$R^1$, $R^2$, $R^3$ and $R^4$ each are independently hydrogen, halogen, $C_{1-4}$ alkyl, $C_{1-4}$ alkoxy or trifluoromethyl;
R is $C_{1-7}$ alkyl, $C_{3-6}$ cycloalkyl, fluoromethyl, difluoromethyl, trifluoromethyl;
A is

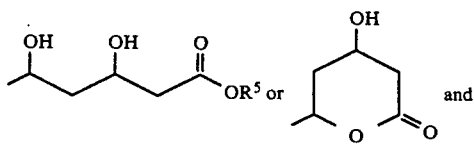

$R^5$ is hydrogen, a hydrolyzable ester group or a cation to form a non-toxic pharmaceutically acceptable salt, are novel antihypercholesterolemic agents which inhibit cholesterol biosynthesis. Intermediates and processes for their preparation are disclosed.

14 Claims, No Drawings

ANTIHYPERCHOLESTEROLEMIC ALKYLENE COMPOUNDS

This application is a continuation of application Ser. No. 236,579, filed Aug. 25, 1988.

BACKGROUND OF THE INVENTION

1. Field of the Invention

The present invention provides novel tetra substituted olefin compounds which are potent inhibitors of the enzyme 3-hydroxy-3-methylglutaryl coenzyme A (HMG-CoA) reductase and, therefore, are useful in the treatment or prevention of hypercholesterolemia, hyperlipoproteinemia and atherosclerosis. The present invention also provides novel processes for the preparation of the tetra substituted olefin compounds and to certain intermediates in their preparation.

2. Disclosure Statement

The natural fermentation products Compactin (R=H) disclosed by A. Endo, et al. in *Journal of Antibiotics*, 29, 1346–1348 (1976) and Mevinolin (R=CH₃) disclosed by A. W. Alberts, et al. in *J. Proc. Natl. Acad. Sci. U.S.A.* 77, 3957 (1980) are very active antihypercholesterolemic agents which limit cholesterol biosynthesis by inhibiting the enzyme HMG-CoA reductase, the rate-limiting enzyme and natural point of cholesterogenesis regulation in mammals, including man. Compactin (R=H) and Mevinolin (R=CH₃; also known as lovastatin) have the structures shown below:

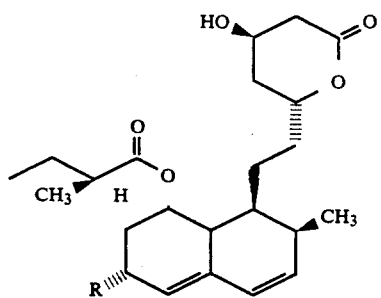

compactin, R=H
mevinolin, R=CH₃

A number of structurally related synthetic compounds useful in the treatment of hypercholesterolemia have also been disclosed in patents and other publications. The synthetic art most closely related is as follows:

U.S. Pat. No. 4,198,425, issued Apr. 15, 1980 to S. Mistui, et al. describes novel mevalonolactone derivatives useful for the treatment of hyperlipidemia and having the general formula

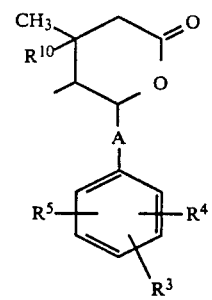

wherein A represents a direct linkage, methylene, ethylene, trimethylene or vinylene group and $R^3$, $R^4$ and $R^5$ represent various substituents.

International patent application WO 84/02131 published June 7, 1984 describes analogs of mevalonolactone having the structure

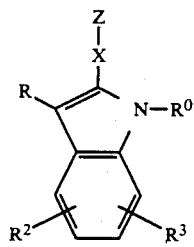

wherein: one of R and $R^0$ is

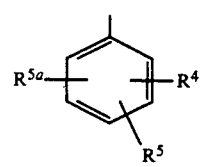

and the other is primary or secondary $C_{1-6}$ alkyl, $C_{3-6}$ cycloalkyl or phenyl—$(CH_2)_n$—;
X is —$(CH_2)_n$— or —CH=CH—;
n is 0, 1, 2 or 3;
Z is

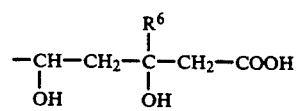

and
$R^4$, $R^5$, $R^{5a}$ and $R^6$ represent various substituents.

International patent application WO 84/02903 published Aug. 2, 1984 describes mevalonolactone analogs having the structures

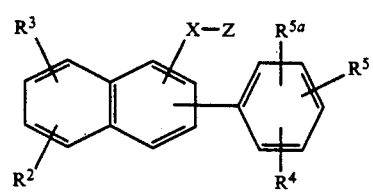

IA

-continued

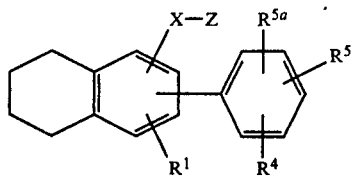

wherein X is —(CH$_2$)$_n$—,

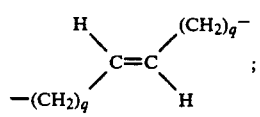

n=0, 1, 2, or 3 and both q's are 0 or one is 0 and the other is 1 and

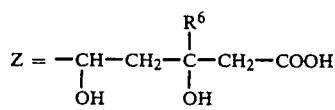

In *J. Med. Chem.*, 28, 347–358 (1985), G. E. Stokker, et al. report the preparation and testing of a series of 5-substituted 3,5-dihydroxypentanoic acids and their derivatives.

In *J. Med. Chem.*, 29, 159–169 (1986), W. F. Hoffman, et al. describe the preparation and testing of a series of 7-(substituted aryl)-3,5-dihydroxy-6-heptenoic (heptanoic) acids and their lactone derivatives. One of the preferred compounds in the reported series has the structure

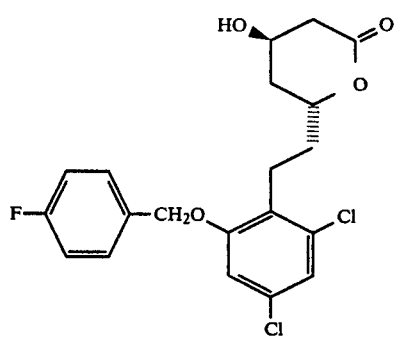

In *J. Med. Chem.*, 29. 170–181 (1986), G. E. Stokker, et al. report the synthesis of a series of 7-[3,5-disubstituted (1,1'-biphenyl)-2-yl]-3,5-dihydroxy6-heptenoic acids and their lactones. Two of the preferred compounds reported in this article have the structures

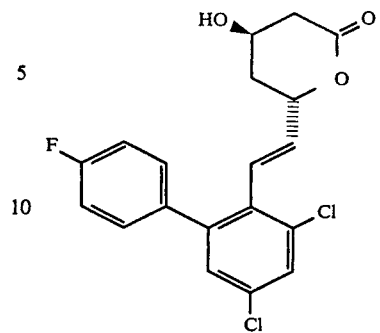

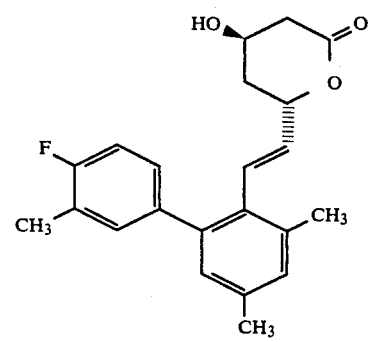

U.S. Pat. No. 4,613,610, issued Sept. 23, 1986 to J. R. Wareing describes pyrazole analogs of mevalonolactone and its derivatives useful for the treatment of hyperlipoproteinemia and atherosclerosis and having the general formula

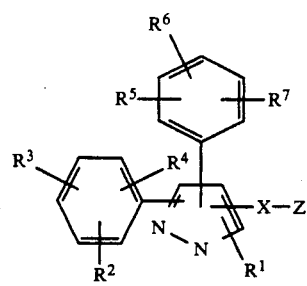

wherein X is —(CH$_2$)$_n$—, —CH=CH—, —CH=CH—CH$_2$— or —CH$_2$—CH=CH—; n is 0, 1, 2 or 3, and R$^1$, R$^2$, R$^3$, R$^4$, R$^5$, R$^6$, R$^7$ and Z represent various substituents.

International patent application WO 86/07054 published Dec. 4, 1986 describes imidazole analogues of mevalonolactone having the general formula

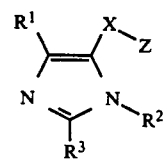

wherein R$^1$, R$^2$ and R$^3$ are C$_{1-6}$ alkyl not containing an asymmetric carbon atom, C$_{3-7}$ cycloalkyl, adamantyl-1 and R$^3$ may also be styryl or R$^1$, R$^2$ and R$^3$ are

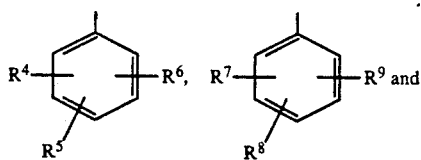

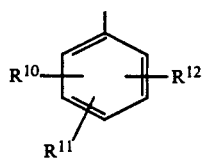

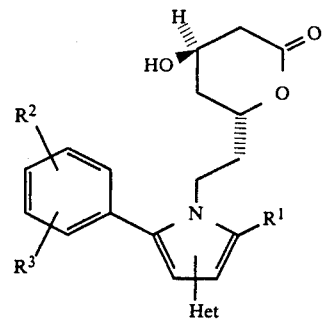

respectively, wherein $R^4$ to $R^{13}$ are various substituents;
X is $-(CH_2)_m-$, $-CH=CH-$, $-CH=CH-CH_2$ or $-CH_2-CH=CH_2-$
wherein
m is 0, 1, 2 or 3 and
Z is

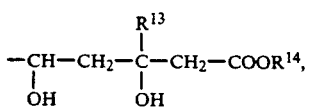 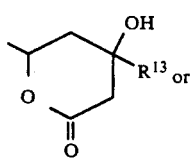 or

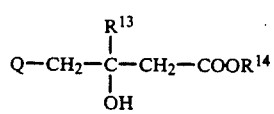

U.S. Pat. No. 4,681,893 issued July 21, 1987 to B. D. Roth describes certain pyrrol-1-yl compounds which are useful as hypochloesterolemic and hypolipidemic agents having the general formula

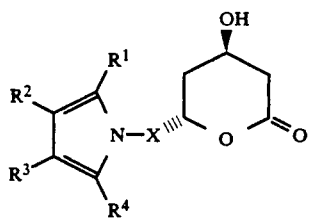

wherein X is $-CH_3-$, $-CH_2CH_2-$, $-CH_2CH_2CH_2-$, or $CH_2CH(CH_3)-$; and $R^1$, $R^2$, $R^3$ and $R^4$ represents various substituents.

U.S. Pat. No. 4,735,958 issued Apr. 5, 1988 to B. D. Roth et al describes certain pyrrol-1-yl compounds which are useful as hypocholesterolemic and hypolipidemic agent having the general formula

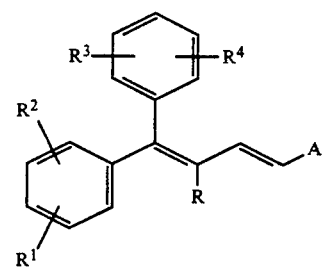

wherein $R^1$, $R^2$, $R^3$ and Het represent various substituents.

SUMMARY OF THE INVENTION

This invention provides novel compounds having the formula

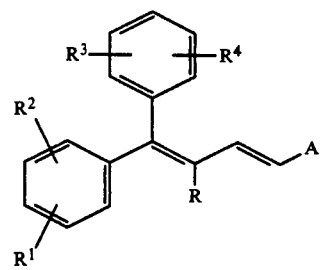

I wherein R, $R^1$, $R^2$, $R^3$, and $R^4$ are as defined below, which are potent inhibitors of the enzyme 3-hydroxy-3-methylglutaryl coenzyme A (HMG-CoA) reductase and are useful in the treatment of hypercholesterolemia, hyperlipoproteinemia and atherosclerosis. The present invention also provides useful intermediates, processes for their preparation and processes for the preparation of compounds of the Formula I.

DESCRIPTION OF THE INVENTION The present invention provides novel tetra substituted olefin compounds which are inhibitors of the enzyme HMG-CoA reductase, which are useful in the treatment of hypercholesterolemia, hyperlipoproteinemia and atherosclerosis, and which have the formula

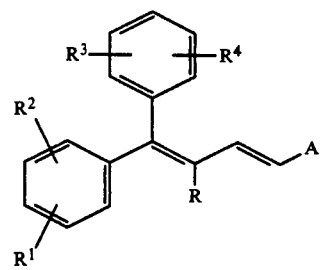

I wherein
$R^1$, $R^2$, $R^3$ and $R^4$ each are independently hydrogen, halogen, $C_{1-4}$ alkyl, $C_{1-4}$ alkoxy or trifluoromethyl;
R is $C_{1-7}$ alkyl, $C_{3-6}$ cycloalkyl, fluoromethyl, difluoromethyl or trifluoromethyl;
A is

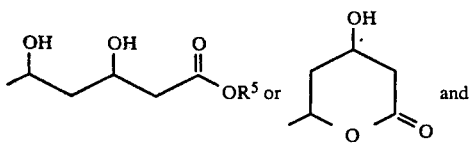

R[5] is hydrogen, a hydrolyzable ester group or a cation to form a non-toxic pharmaceutically acceptable salt.

This invention also provides processes for the preparation of the compounds of Formula I and to intermediates in the preparation of compounds of Formula I.

The terms "$C_{1-4}$ alkyl", "$C_{1-6}$ alkyl" and "$C_{1-4}$ alkoxy" as used herein and in the claims (unless the context indicates otherwise) mean unbranched or branched chain alkyl or alkoxy groups such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine while the term "halide" as used herein and in the claims is intended to include chloride, bromide and iodide anion. The term "a cation to form a non-toxic pharmaceutically acceptable salt" as used herein and in the claims is intended to include nontoxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been used to form salts of carboxylic acids. Unless otherwise specified, the term "a hydrolyzable ester group" as used herein and in the claims is intended to include an ester group which is physiologically acceptable and hydrolyzable under physiological conditions such as $C_{1-6}$ alkyl, phenylmethyl and pivaloyloxymethyl.

In the compounds of Formula I, it is intended that all of the double bonds are in the trans configuration, i.e., (E), as indicated in the structural formulae used herein and in the claims.

As the compounds of the present invention may possess one or two asymmetric carbon atoms, the invention includes all of the possible enantiomeric and diastereomeric forms of the compounds of Formula I as described herein and in the claims. The compounds of Formula I which contain two centers of asymmetry may produce four possible stereoisomers designated as the RR, RS, SR and SS enantiomers; all four stereoisomers are considered within the scope of this invention. Specifically, the compounds of Formula I having two asymmetric carbon atoms bearing the hydroxy groups in the 3 and 5 position may produce four possible stereoisomers which are designated as the (3R,5S, (3S,5R), (3R,5R) and (3S,5S) stereoisomers. As used herein and in the claims, the term "(±)-erythro" is intended to include a mixture of (3R,5S) and (3S,5R) enantiomers, and the term "(±)-threo" is intended to include a mixture of (3R,5R) and (3S,5S) enantiomers. The use of a single designation such as (3R,5S) is intended to include mostly one stereoisomer. The lactone forms of the compounds of Formula I also have two asymmetric carbon atoms at the 4 and 6 position, and the resulting four stereoisomers may be designated as the (4R,6S), (4S,6R), (4R,6R) and (4S,6S) stereoisomers. As used herein and in the claims, the term "trans" lactone is intended to include a mixture of (4R,6S) and (4S,6R) enantiomers while the term "cis" lactone is intended to include a mixture of (4R,6R) and (4S,6S) enantiomers. Mixtures of isomers can be separated into individual isomers according to methods which are known per se. e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The possible enantiomeric forms may also be separated by fractionation through chiral high pressure liquid chromatography columns.

If it is desired to prepare the (+) isomer of the compounds of Formula I, then the synthetic (±) isomer of the present invention may be resolved by resolution methods well-known to those skilled in the art. For example of a resolution procedure in this general class of compounds, U.S. Pat. No. 4,375,475 issued Mar. 1, 1983 to A. K. Willard, et al. describe the resolution of a racemic (±) trans lactone with excess d-(+)-α-methylbenzylamine (or the corresponding l-(−)-α-methylbenzylamine), separating the resulting two diastereoisomeric amines and hydrolyizng to the corresponding, for example, sodium salt. The resulting salt may then be converted by conventional means to the corresponding acid, ester and lactone. Preferably, the optically active enantiomers of the compounds of Formula I may be prepared by stereoselective synthetic procedures, some of which are described herein. The use of optically active reagents in combination with the appropriate intermediate described herein would produce the desired enantiomer of the compound of Formula I.

Since the compounds of Formula I may contain varying amounts of solvent as ascertained mainly by elemental analysis, the present invention is intended to include solvates of the compounds of Formula I. In some cases, it appears that the products may be true solvates, while in other cases, the products may merely retain adventitious solvent or be a mixture of solvate plus some adventitious solvent. Preferably, the solvate is water and, most preferably, one to three moles of water. The examples below give the amount of solvent where appropriate in the analysis and melting points are those of the solvated product unless otherwise indicated.

In the compounds of Formula I, R[1], R[2], R[3],and R[4], independently, are preferably hydrogen, fluoro, chloro, methyl or methoxy, and most preferably, R[1] and R[3] are hydrogen and R[2] and R[4], independently, are hydrogen, fluoro, methyl or methoxy. It is preferred that R is methyl, ethyl, propyl, 1-methylethyl, 1,1-dimethylethyl, trifluoromethyl, cyclopropyl or cyclohexyl and more preferably R is ethyl, 1-methylethyl, 1,1-dimethylethyl or cyclopropyl. Preferably, R[5] is hydrogen, $C_{1-6}$ alkyl or a pharmaceutically acceptable cation. Most preferably, R[5] is a pharmaceutically acceptable cation especially sodium or potassium.

In the compounds of Formula I wherein A contains two asymmetric carbon atoms bearing the hydroxy group, the erythro isomer is preferred and the (3R,5S) isomer being most preferred. In the compounds of Formula I wherein A contains two asymmetric carbon atoms in the lactone form, the trans isomer is preferred and the (4R,6S) isomer being most preferred.

The compounds of Formula I may be prepared by various procedures, preferably starting from a compound of Formula II

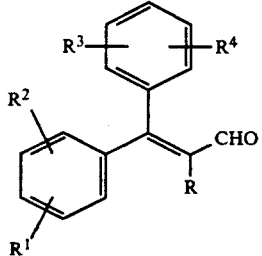

II wherein $R^1$, $R^2$, $R^3$ and $R^4$ each are independently hydrogen, halogen, $C_{1-4}$ alkyl, $C_{1-4}$ alkoxy or trifluoromethyl; and R is $C_{1-7}$ alkyl, $C_{3-6}$ cycloalkyl, fluoromethyl, difluoromethyl or trifluoromethyl.

The compounds of Formula IIa (compounds of Formula II wherein R is $C_{1-7}$ alkyl or $C_{3-6}$ cycloalkyl) may be prepared from the optionally substituted benzophenones III by aldol condensation and dehydration of the aldohol V to the tetra substituted olefin VI followed by reduction of the ester group in compound VI with subsequent oxidation of the resulting alcohol VII, as shown in Reaction Scheme 1.

Reaction Scheme 1

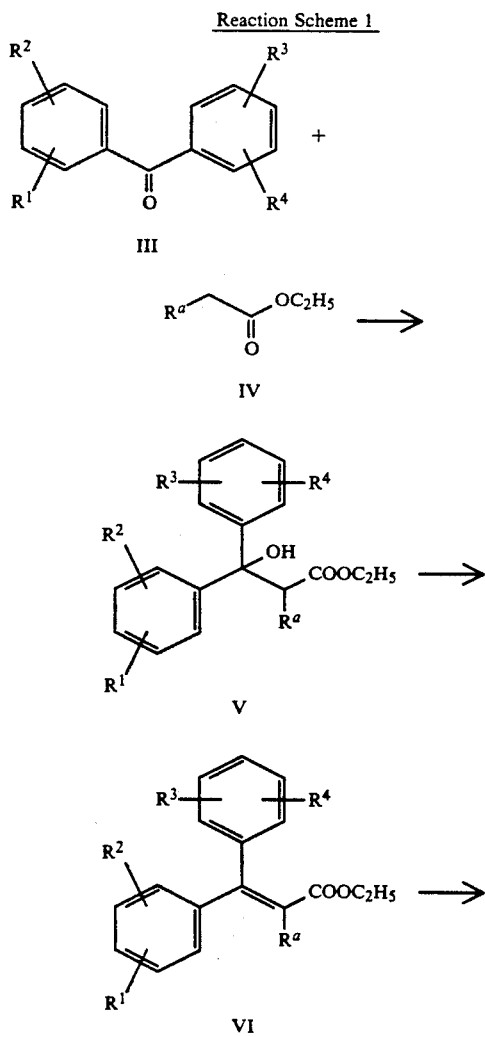

-continued
Reaction Scheme 1

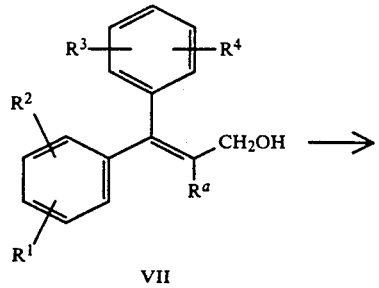

VII

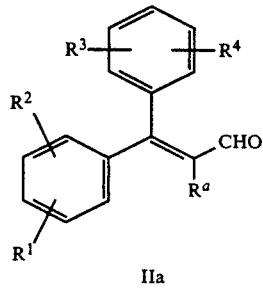

IIa

In Reaction Scheme 1, $R^a$ is $C_{1-7}$ alkyl or $C_{3-7}$ cycloalkyl, $R^1$, $R^2$, $R^3$ and $R^4$ are as previously defined. The optionally substituted benzophenones of the Formula III may be prepared by the general and well-known Friedel Crafts reaction of a substituted phenyl catalyzed by Lewis acids, e.g., with aluminum chloride in carbon tetrachloride at about 0° C. A large number of substituted benzophenones are known and their prepartion are described in the art while many others are commercially available. For example, many of the starting materials of Formula III are described by G. Olah in *Friedel-Cratts and Related Reactions*, Vol. 3. Part 1 and 2, Interscience Publishers, New York, 1964 and references therein. The Friedel Crafts reaction may produce a mixture of benzophenones and, if so produced, the mixture may be separated by conventional techniques known in the art.

The appropriate benzophenone of the Formula III may be treated with the desired substituted acetate ester of Formula IV in the presence of a strong base such as lithium diisopropylamide and lithium N-isopropylcyclohexylamide in an inert organic solvent, e.g., tetrahydrofuran, diethyl ether, 1,2-dimethoxyethane and the like at low temperatures of from about −20° C. to about −78° C. The tertiary alcohols of Formula V may then be dehydrated by conventional dehydration procedures until the production of the tetra substituted olefin VI is essentially complete. The dehydration may be carried out by heating the alcohol of Formula V in a suitable inert organic solvent, e.g., toluene, benzene or xylene with a small amount of organic or mineral acid such as p-toluenesulfonic acid or sulfuric acid in the presence of a drying agent, e.g., $Na_2SO_4$, $MgSO_4$, molecular sieves, etc., or preferably, the water which is produced is azeotropically removed with a Dean-Stark trap or similar apparatus. Alternatively, the alcohol of Formula V may simply be heated with potassium hydrogen sulfate at temperatures of about 190° C.

The alkylene ester of the Formula VI may then be converted by standard techniques to the alcohol VII by a series of known reactions. According to one reaction route, the compound of Formula VI may first be hydrolyzed by conventional methods, such as base hydrolysis, i.e., lithium hydroxide, potassium hydroxide and sodium hydroxide. The resulting acid would then be converted to an acyl chloride by reacting with a reagent such as oxalyl chloride in methylene chloride at reflux temperature and the resulting acyl chloride would be reduced with a reducing agent, preferably, lithium aluminum hydride in tetrahydrofuran at −78° C. to produce an alcohol of the Formula VII. Alternatively, and more preferably, the alcohol VII may be prepared in one step from the corresponding ester VI by reduction with reducing agents such as diisobutylaluminum hydride in a non-reducible inert solvent such as methylene chloride, at low temperatures, preferably at about −78° C.

The allylic alcohol of Formula VII may be readily oxidized by conventional oxidizing agents such as pyridinium chlorochromate in a non-reactive solvent, preferably, methylene chloride at ambient temperature to produce the corresponding allylic aldehydes of Formula IIa.

The compounds of Formula IIb (compounds of Formula II wherein R is fluoromethyl, difluoromethyl or trifluoromethyl) may be prepared from a substituted propene of Formula VIII which is itself prepared from an optionally substituted benzophenones III, an aldehyde of Formula IIc or an allylic alcohol of Formula VIIa. The compound of Formula VIII may then be converted to the allylic bromide of Formula IX followed by oxidation to produce the aldehydes of Formula IIb, as shown in Reaction Scheme 2.

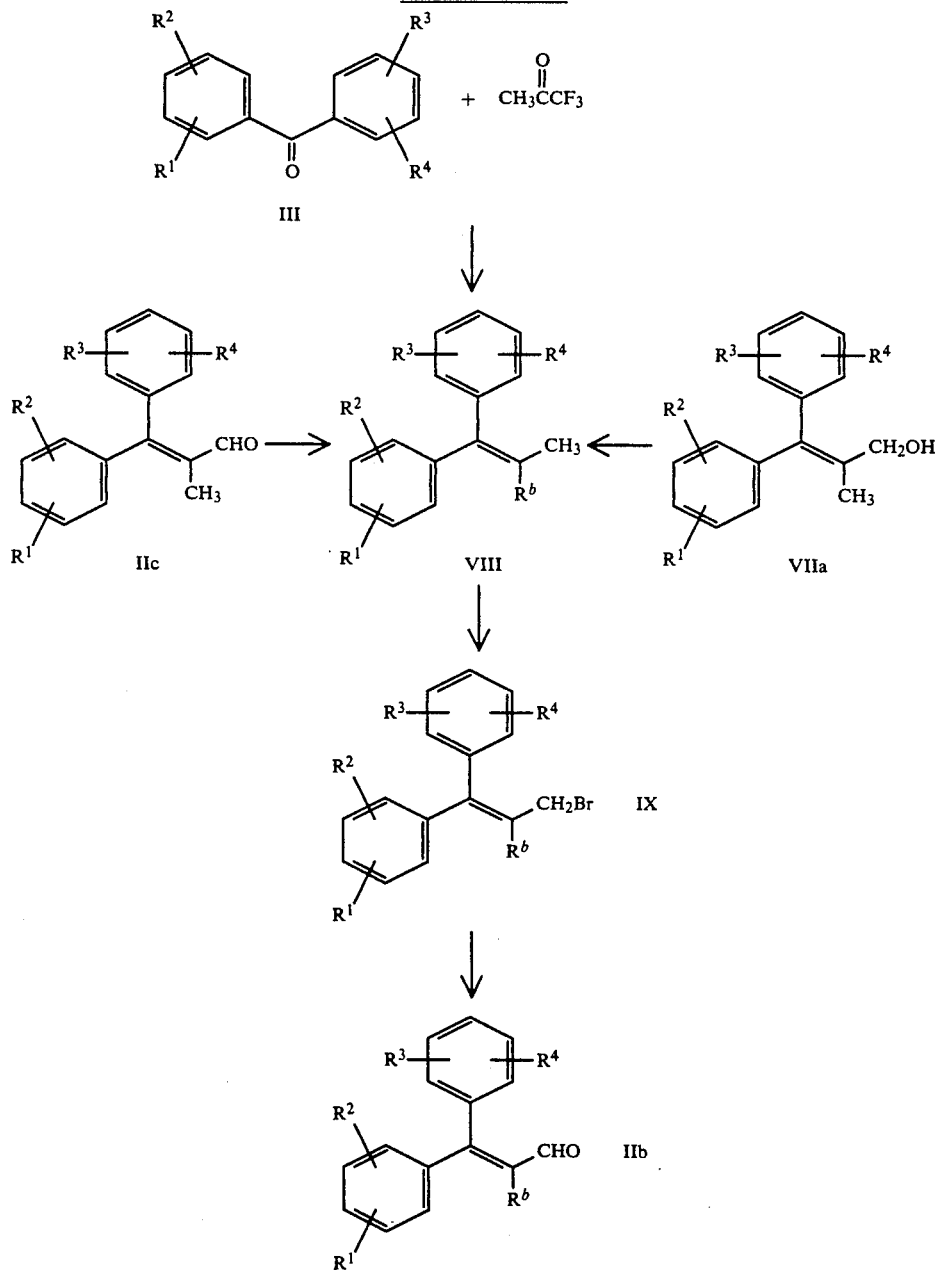

In Reaction Scheme 2, $R^b$ is fluoromethyl, difluoromethyl or trifluoromethyl, $R^1$, $R^2$, $R^3$ and $R^4$ are as previously defined. When it is desired to prepare a compound of Formula VIII wherein R^b is trifluoromethyl then the appropriate benzophenone of Formula III is treated with 1,1,1-trifluoroacetone in a non-reactive solvent preferably in tetrahydrofuran in the presence of titanium trichloride and lithium. If it is desired to prepare a compound of Formula VIII wherein R^b is difluoromethyl then an aldehyde of Formula IIc which is itself prepared as shown in Reaction Scheme 1 may be treated with diethylaminosulfur trifluoride at about ambient temperature to produce the difluoromethyl compound of Formula VIII. Additionally, the allylic alcohol of Formula VIIa may be treated with diethylaminosulfur trifluoride to produce a compound of Formula VIII wherein R^b is fluoromethyl.

The compounds of Formula IIb may be prepared from the compounds of Formula IX by first treating the compounds of Formula VIII with N-bromosuccinimide in the presence of a catalyst such as azaisobutyric dinitrile or benzoyl peroxide in carbon tetrachloride, and then reacting the resulting allylic bromide of Formula IX with 2-nitropropane by the general procedure described herein and in *Org. Syn. Coll.* Vol. IV. 932. If the reaction with 2-nitropropane is not complete then the mixture of desired aldehyde and allylic alcohol may be treated with activated manganese dioxide to complete the reaction to the desired aldehyde of Formula IIb as described in Example 74.

The compounds of Formula I may be prepared from a novel aldehyde of the Formula II wherein R^6 is a hydrolyzable ester group and R, R^1, R^2, R^3 and R^4 are as previously defined by the general reaction route shown in Reaction Scheme 3.

Reaction Scheme 3

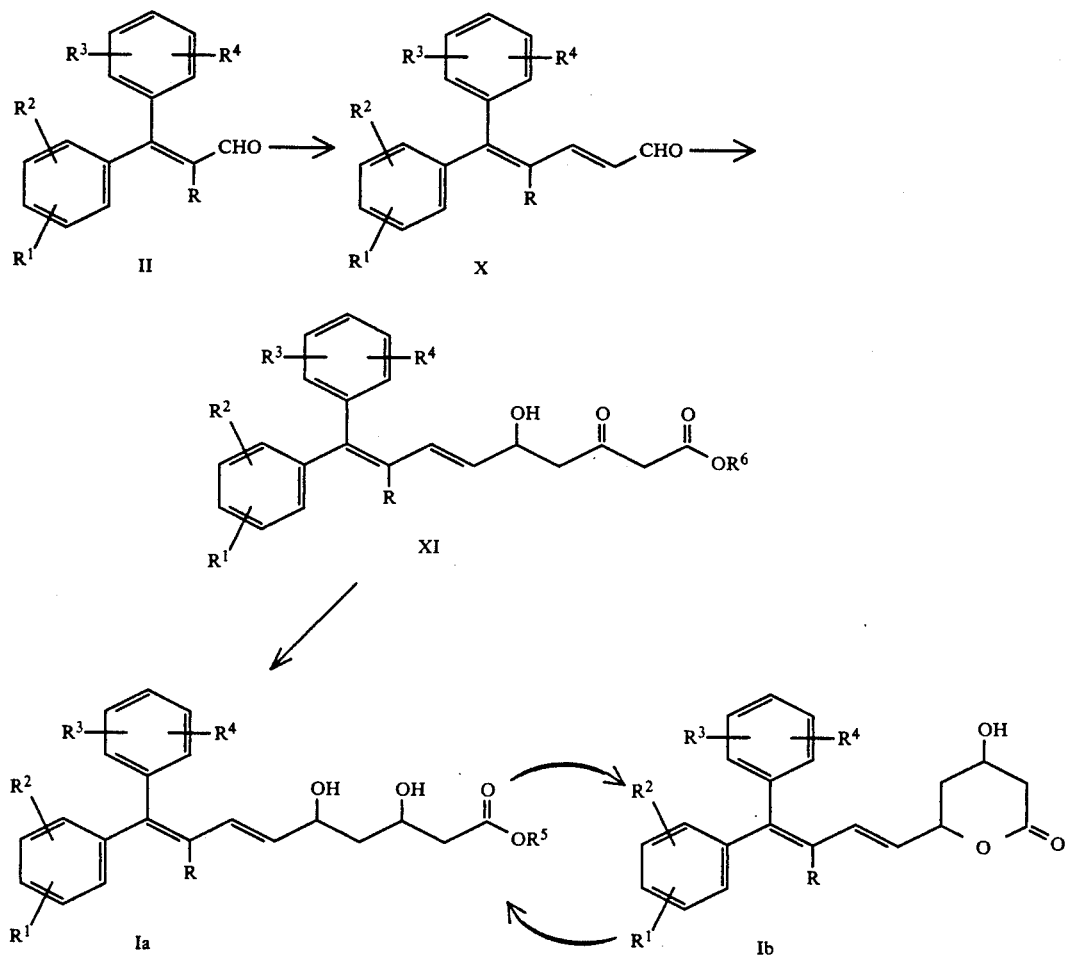

In Reaction Scheme 3, an allylic aldehyde of Formula II may be treated with N-ethylidenecyclohexanamine and a strong base such as lithium diisopropylamide in a non-reactive solvent such as benzene, toluene, tetrahydrofuran, 1,2-dimethoxyethane and the like. The reaction can be conducted at a temperature of about $-70°$ C. to about $0°$ C. and preferably from about $-70°$ C. to $-40°$ C. until the reaction is essentially complete. It should be understood and appreciated by those skilled in the art that at least one equivalent of N-ethylidenecyclohexanamine per equivalent of a compound of Formula II is necessary. Preferably, the reaction is conducted with an excess of reagent under controlled reaction conditions.

The penultimate intermediate of Formula XI wherein R^6 is a hydrolyzable ester group such as methyl, ethyl and t-butyl ester may be prepared from the corresponding aldehyde of Formula X by reaction with the dianion of acetoacetate ester generated in situ, for example, as described in Example 6. The reaction may be conducted in an inert organic solvent such as tetrahydrofuran at low temperatures from $-78°$ C. to about $0°$ C. and preferably from about $-78°$ C. to $-40°$ C. until the reaction is essentially complete. The ketone ester of Formula XI may be reduced to the dihydroxy ester of Formula Ia by reduction of the ketone radical with reducing agents well-known in the art, e.g., sodium borohydride, sodium cyanoborohydride, zinc borohydride, disiamylborane, diborane, ammonia borane, t-butylamine borane, pyridine borane, lithium tri-s-butylborohydride or other similar reducing agents which will not reduce nor hydrolyze the carboxylic ester radical. Preferably, the reduction is carried out in a stereospecific manner by a two-step stereospecific reduction in order to maximize the production of the preferred erythro isomer of the compound of Formula I. The stereospecific reduction of a compound of Formula XI is carried out with trisubstituted alkylboranes, preferably triethylborane, or alkoxydialkylboranes, preferably methoxydiethylborane or ethoxydiethylborane, [*Tetrahedron Letters*, 28. 155 (1987)] at a temperature of about $-70°$ C. to about ambient temperature. The complex which is produced is then reduced with sodium borohydride at a temperature of about $-50°$ C. to about $-78°$ C. in an inert organic solvent such as tetrahydrofuran, diethyl ether and 1,2-dimethoxyethane, preferably, tetrahydrofuran. The reduction is then completed by the addition of methanol. The resulting compound of Formula Ia produced from the stereospecific reduction contains two asymmetric carbon atoms bearing the hydroxy group in an erythro configuration. Thus, reduction of the ketone radical under the conditions employed herein produces mostly the erythro isomers of the compounds of Formula Ia and only a small amount of the less preferred threo isomers. The ratio of erythro-threo isomers produced will vary according to the specific compound utilized and the reaction conditions employed. Normally, this ratio will be approximately 9:1 to 9.8 : 0.2. However, the use of a non-specific reduction will normally produce a 1:1 mixture of isomers. Nevertheless, the mixture of isomers may be separated and purified by conventional techniques and then converted to the compounds of general Formula I in a conventional manner well-known to those skilled in the art.

The preparation of a compound of Formula Ia wherein $R^5$ is a cation is preferably carried out by base hydrolysis of a compound of Formula Ia wherein $R^5$ is a hydrolyzalable ester group with bases such as sodium hydroxide, potassium hydroxide and lithium hydroxide in an organic solvent such as tetrahydrofuran, ethanol and methanol at a temperature from $0°$ C. to about $50°$ C. The form of the cation is normally determined by the corresponding cation of the hydroxide employed. However, if desired, the cation may be exchanged for another cation by treatment with ion-exchange resins.

The compound of Formula Ia may be cyclized to the corresponding lactone of Formula Ib by conventional lactonization methods, for example, by heating the acid in an inert organic solvent such as benzene, toluene and xylene and azetropically removing the water which is produced or by treating the compound of Formula Ia in an inert organic solvent, e.g., toluene, benzene, diethyl ether or methylene chloride with an acid such as p-toluenesulfonic acid, in the presence of a drying agent, e.g., NaSO4, MgSO4 or molecular sieves. Preferably, the lactonization may be carried out by activation of the carboxyl radical with a carbodiimide in an inert organic solvent such as tetrahydrofuran, and preferably, in methylene chloride or ethyl acetate at about ambient temperature to produce the lactone of Formula Ib. If the relative stereochemical configuration of the two carbon atoms bearing the hydroxy groups are established as erythro in Formula Ia, then the lactonization will produce the preferred trans lactone of Formula Ib, otherwise the lactonization will produce a mixture of trans and cis lactones. The resulting lactone of Formula Ib may, if desired, be hydrolyzed with base or acid to produce the compounds of Formula Ia.

In an alternate reaction route, the preparation of compounds of Formula I may be prepared from intermediates of Formula XIII, as shown in Reaction Scheme 4.

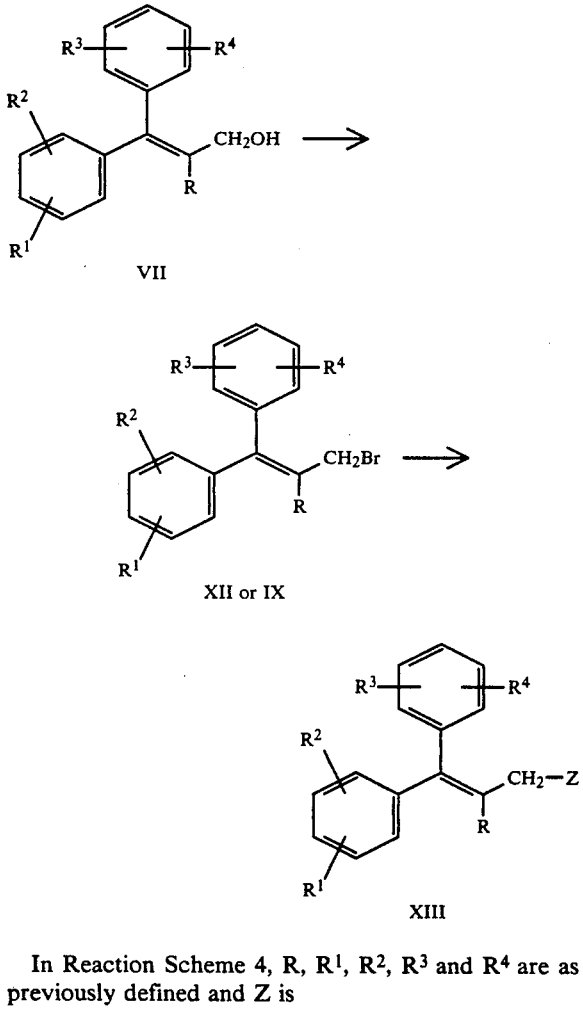

Reaction Scheme 4

In Reaction Scheme 4, R, $R^1$, $R^2$, $R^3$ and $R^4$ are as previously defined and Z is

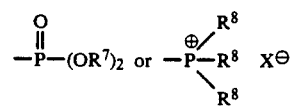

in which $R^7$ is $C_{1-4}$ alkyl, $R^8$ is phenyl which is unsubstituted or substituted by one or two $C_{1-4}$ alkyl or chloro substituents and X is bromo, chloro or iodo. The allylic bromide of Formula XII, wherein R is $R^a$, may be prepared from the alcohol of Formula VII, wherein R is $R^a$, by treatment with carbon tetrabromide and triphenylphosphine while the allylic bromide of Formula IX, wherein R is $R^b$, may be prepared as shown in Reaction Scheme 2.

The allylic bromide of Formula XII or IX may be reacted in a conventional manner with phosphines such as triphenylphosphine in an inert organic solvent such as cyclohexane to produce the phosphonium salt of Formula XIII. Alternatively, the allylic bromide of Formula XII or IX may be reacted in a conventional manner with phosphites such as trimethyl phosphite and triethyl phosphite either neat or in an inert organic solvent, and preferably, neat to produce the phosphonates of Formula XIII.

The compounds of Formula I may be prepared from an intermediate of Formula XIII by the reaction with aldehyde intermediates well known to those skilled in the art. The phosphonium salt or phosphonate of Formula XIII may be reacted with silyl protected aldehydes in a similar manner as described in *Tetrahedron Letters.* 25. 2435 (1984) and U.S. Pat. No. 4,571,428 to produce erythro compounds of Formula Ia. A compound of Formula XIII may also be reacted with optically active aldehydes as described in *Tetrahedron Letters.* 23. 4305 (1982) and U.S. Pat. No. 4,613,610 to produce the (4R,6S) enantiomer of a compound of Formula Ib which can, if desired, be converted to the (3R, 5S) enantiomer of a compound of Formula Ia. The methods described above as well as other methods are described in U.S. Patent Application Ser. No. 151,513 filed Feb. 18, 1988 by one of us and a colleague.

When it is desired to prepare mostly one stereoisomer of a compound of Formula I, it is preferred to employ optically pure starting materials. The various procedures which may be used to prepare one isomer of a compound of Formula I is illustrated in Reaction Schemes 5 and 6. The most preferred isomer of a compound of Formula I wherein A is defined as

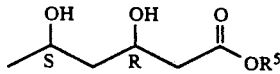

is the (3R, 5S) isomer, and the most preferred isomer of a compound of Formula I wherein A is defined as

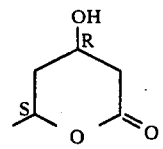

is the (4R,6S) isomer. It should be appreciated that it is necessary to have only one of the above definitions of A for compounds of Formula I since they may be interconverted as shown in Reaction Scheme 3. To illustrate the use of optically pure starting materials, the preparation of a preferred embodiment of compounds of Formula I such as the (3R,5S) isomer of compounds of Formula Ia and the (4R, 6S) isomer of compounds of Formula Ib is shown in Reaction Scheme 6.

Another particularly preferred method envisioned for the preparation of compounds of the Formula Ia and Ib of the present invention is the use of intermediates having the formulae

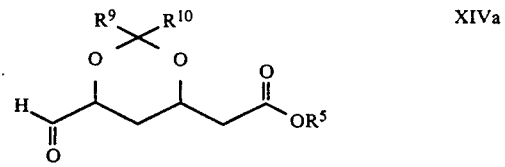

XIVa

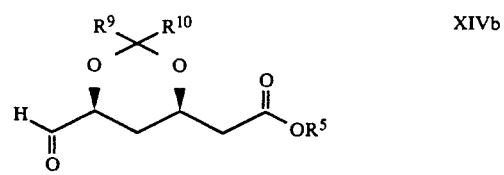

XIVb in substantially the cis form wherein $R^9$ and $R^{10}$ each are $C_{1-4}$alkyl or $R^9$ and $R^{10}$, taken together with the carbon atom to which they are attached, is cyclopentyl, cyclohexyl or cycloheptyl and $R^{10}$ is hydrogen, $C_{1-4}$alkyl or a metal cation. The preparation and use of the compounds of Formulae XIVa and XIVb is described herein and in U.S. Pat. Application Ser. No. 156,865, filed Feb. 18, 1988 by William T. Han and John J. Wright. The use of the intermediates of Formula XIVa and Formula XIVb is shown in Reaction Schemes 5 and 6, respectively.

Reaction Scheme 5

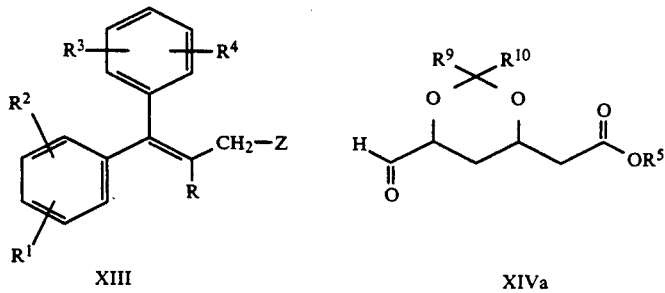

XIII         XIVa

Reaction Scheme 5
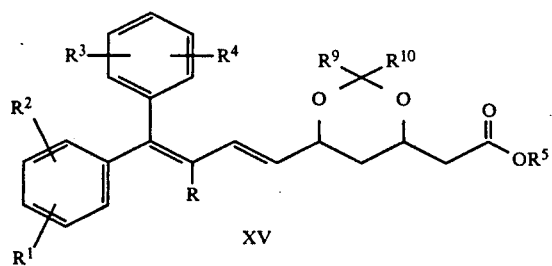
XV
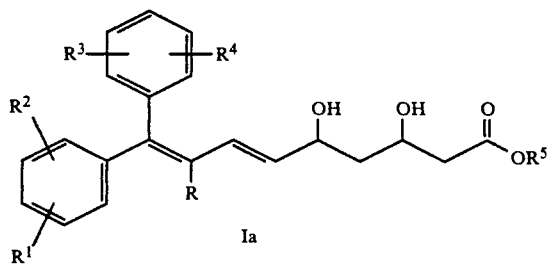
Ia
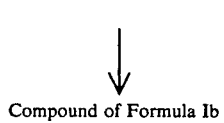
Compound of Formula Ib
Reaction Scheme 6
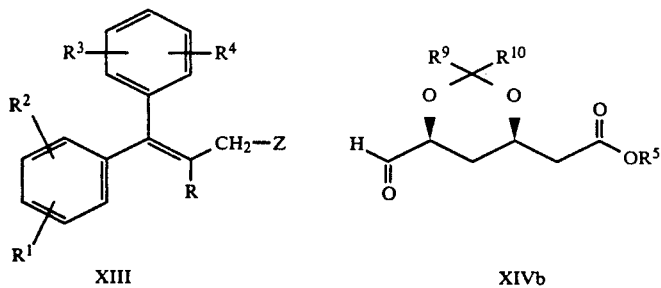
XIII     XIVb
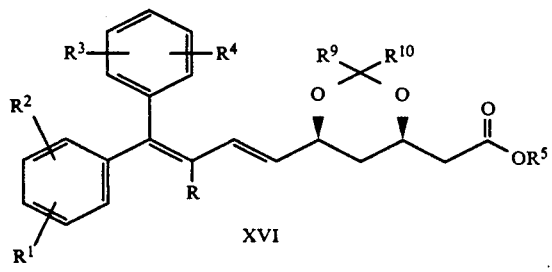
XVI

Reaction Scheme 6

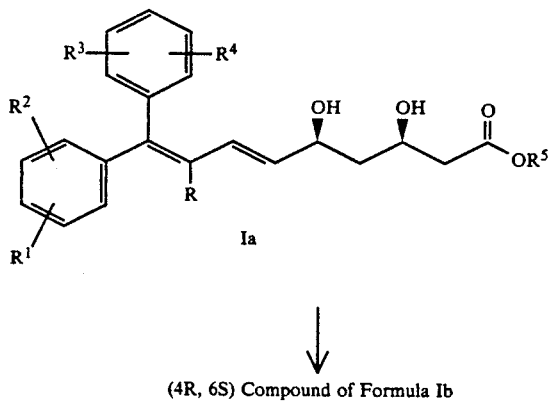

↓

(4R, 6S) Compound of Formula Ib

In Reaction Schemes 5 and 6, R, $R^1$, $R^2$, $R^3$, $R^4$ and $R^5$, are as previously defined; Z is

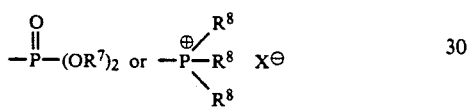

in which $R^7$ is $C_{1-4}$alkyl, $R^8$ is phenyl which is unsubstituted or substituted by one or two $C_{1-4}$alkyl or chloro substituents; X is bromo, chloro or iodo and $R^9$ and $R^{10}$ each are independently hydrogen, $C_{1-6}$alkyl or phenyl which is optionally substituted by one or two $C_{1-4}$alkyl, halogen, $C_{1-4}$alkoxy or trifluormethyl. The preparation of the phosphonium salt and the phosphonate of Formula XIII is shown in Scheme 4. The reaction of a compound of Formula XIII with a compound of Formula XIVa or Formula XIVb to produce a compound of Formula XV or XVI, respectively, wherein $R^5$ is $C_{1-4}$alkyl may be carried out in an inert organic solvent such as tetrahydrofuran and N,N-dimethylformamide in the presence of a strong base such as n-butyllithium at a temperature of about $-50°$ C., to about $-78°$ C. When the reaction of a compound of Formula XIII is carried out with a compound of Formula XIVa or XIVb wherein $R^5$ is hydrogen, it is preferred to use two equivalents of a strong base such as n-butyllithium. Alternatively, the salt of a compound of Formula XIVa or XIVb may be prepared which is then treated with a compound of Formula XIII and a strong base. The methods of addition, salt formation and ylide preparation are well-known to those skilled in the art. The alkylene compounds of Formula XV or XVI may be readily deprotected by well-known procedures such as mild acid, e.g., 0.2N HCl and 0.5N HCl in an inert organic solvent such as tetrahydrofuran to produce the erythro compounds of Formula Ia or the (3R,5S) compounds of Formula Ia which may then be converted to the trans compounds of Formula Ib or (4R,6S) compounds of Formula Ib in a conventional manner well-known to those skilled in the art.

In a preferred embodiment of the invention the compounds of Formula I have the structure

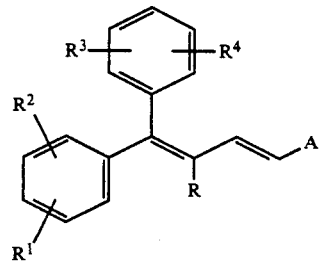

wherein
$R^1$, $R^2$, $R^3$ and $R^4$ each are independently hydrogen, fluoro, chloro, methyl or methoxy;
R $C_{1-7}$ alkyl, $C_{3-6}$ cycloalkyl, fluoromethyl, difluoromethyl or trifluoromethyl;
A is

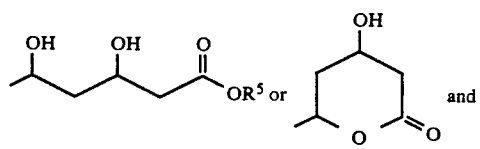

$R^5$ is hydrogen, a hydrolyzable ester group or a cation to form a non-toxic pharmaceutically acceptable salt.

In a more preferred embodiment of the invention the compounds of Formula I have the structure

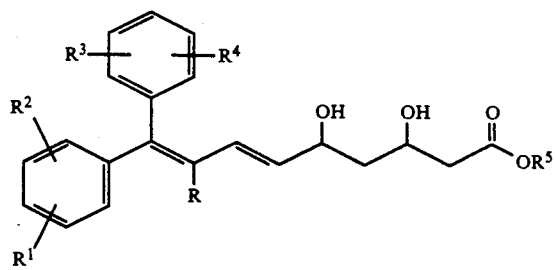

wherein $R^1$, $R^2$, $R^3$, and $R^4$ each are independently hydrogen, fluoro, chloro, or methyl; R is ethyl, 1-methylethyl, cyclopropyl or 1,1-dimethylethyl; and $R^5$ is hydrogen, $C_{1-6}$ alkyl or a cation to form a non-toxic pharmaceutically acceptable salt. In a particularly preferred embodiment, R is 1-methylethyl.

In another more preferred embodiment of the invention the compounds of Formula I have the structure

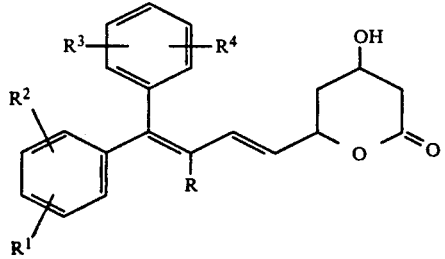

wherein $R^1$, $R^2$, $R^3$, and $R^4$ each are independently hydrogen, fluoro, chloro, or methyl; and R is ethyl, 1-methylethyl, cyclopropyl or 1,1-dimethylethyl. In a particularly preferred embodiment, R is 1-methylethyl.

In another aspect, this invention provides novel intermediates of the formula

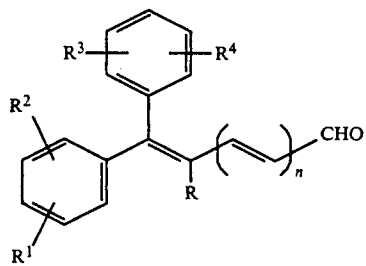

XVII wherein $R^1$, $R^2$, $R^3$ and $R^4$ each are independently hydrogen, halogen, $C_{1-4}$ alkyl, $C_{1-4}$ alkoxy, or trifluoromethyl; n is zero or 1; and R is hydrogen, $C_{1-4}$alkyl or phenyl.

In a preferred embodiment, the compounds of Formula VII have the structure

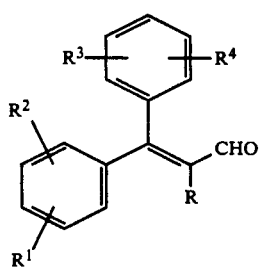

wherein $R^1$, $R^2$, $R^3$ and $R^4$ each are independently hydrogen, fluoro, chloro, or methyl; and R is ethyl, 1-methylethyl, cyclopropyl or 1,1-dimethylethyl.

In another preferred embodiment, the compounds of Formula XVII have the structure

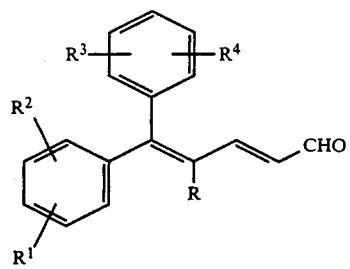

wherein $R^1$, $R^2$, $R^3$ and $R^4$ each are independently hydrogen, fluoro, chloro or methyl; and R is ethyl, 1-methylethyl, cyclopropyl or 1,1-dimethylethyl.

In still another aspect, this invention provides novel intermediates of the formula

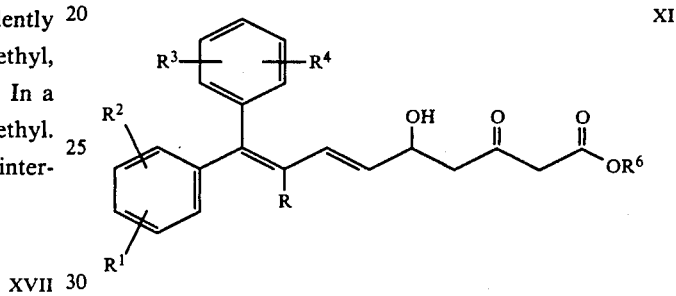

XI wherein $R^1$, $R^2$, $R^3$ and $R^4$ each are independently hydrogen, halogen, $C_{1-4}$alkyl, $C_{1-4}$alkoxy or trifluoromethyl; R is $C_{1-7}$ alkyl, $C_{3-6}$ cycloalkyl, fluoromethyl, difluoromethyl or trifluoromethyl; and $R^6$ is a hydrolyzable ester group.

The compounds of Formula I are competitive inhibitors of the enzyme 3-hydroxy-3-methylglutaryl coenzyme A (HMG-CoA) reductase, the rate limiting enzyme in cholesterol biosynthesis, and therefore, are selective suppressors of cholesterol biosynthesis in animals, including man. Consequently, they are useful in the treatment of hypercholesterolemia, hyperlipoproteinemia and atherosclerosis. The biological activity of the compounds of Formula I may be demonstrated in the following biological tests.

Test A: In Vitro Inhibition of Microsomal HMG-CoA Reductase:

The intact, fully activated microsomal form of rat liver HMG-CoA reductase (subunit MW ca 100,000 daltons) was prepared as described by Parker, et al., Biochem. Biophys. Res. Commun., 125, 629–635 (1984), and used as the source of enzyme for assays. HMG-CoA reductase activity was determined essentially by the method of Shapiro, et al., Biochem. Biophys. Acta., 370. 369–377 (1974), with modifications as described by Ingebritsen and Gibson, Meth. Enzymol. 71. 486–497 (1981) with the exception that the internal standard $^3$H-mevalonolactone is added after termination of the assay. In this procedure, the enzyme is assayed by measuring the formation of product, $^{14}$C-mevalonate, from the substrate, [3-$^{14}$C]-HMG-CoA, in the presence of NADPH. The $^{14}$C-mevalonate is converted to its lactone and isolated by silica thin-layer chromatography (Whatman LK5D, developed in 50:50 benzene:acetone) in the presence of $^3$H-mevalonolactone as an internal standard. Assays were conducted under conditions in which product formation was linear with respect to time and enzyme concentration.

To measure reductase inhibition, test compounds dissolved in water or dimethylsulfoxide and diluted in buffer A (50 mM imidazole-HCl, 250 mM NaCl, 1 mM EDTA, 1 mM EGTA, 5 mM DTT, 20 $\mu$M leupeptin, pH =7.2) were incubated with aliquots of microsomes (80-160 $\mu$g protein in buffer A) followed by addition of d,l-[3-$^{14}$C]-HMG-CoA (0.33 mM, 2.0 dpm/picomole) and NADPH (3.0 mM). The 50 percent inhibitory concentration IC$_{50}$) for each compound in Table 1 was calculated from the linear regression line of the percent decrease (from control) in enzyme activity vs. log concentration of inhibitor, determined using at least 4 dilutions of each test compound assayed in duplicate.

TABLE 1

| Inhibition of Microsomal HMG-CoA Reductase | |
|---|---|
| Compound of Example No. | IC$_{50}$ $\mu$molar |
| 8 | 0.265 |
| 42 | 0.50 |
| 51 | 0.45 |
| 59 | 0.41 |
| 73 | 1.58 |

Test B: Isolated Hepatocyte Cholesterol Biosynthesis Assay:

Intact parenchymal hepatocytes were isolated from male Wistar rats (180-280 g) fed cholestyramine containing or normal diet, using the collagenase perfusion method essentially as described by Seglen, in *Methods in Cell Biology* (D. Prescott, ed.) Vol. 13, pp. 29-83, Academic Press, New York (1976). Cell preparations were used only when viability (trypan blue exclusion) exceeded 90%. Cholesterol biosynthesis was determined as the incorporation by hepatocytes of $^3$H from [$^3$H]-water into total (cellular plus medium) 3$\beta$-hydroxy sterols as per Ingebritsen, et al., *J. Biol. Chem.*, 254, 9986-9989 (1979). Hepatocyte sterols and lipids were isolated by a modification of the methods described by Kates, in *Techniques in Lipidology*. (M. Kates, ed.), pp. 349, 360-363, North Holland Publ. Co., Amsterdam, 1972. To isolate sterols, cells are extracted with methanol:chloroform:water (2:1:0.8), the chloroform phase is separated and extracted with benzene to remove traces of water, then dried under nitrogen. The residue is saponified at 75° C. with 0.30 N NaOH in methanol:water (9:1). The alkaline mixture is then extracted three times with petroleum ether to yield the non-saponifiable lipids which include the free as well as initially esterified cholesterol. The extract is dried under nitrogen in the presence of carrier cholesterol (0.1 mg) and 10% benzene, and the residue is dissolved in acetone:ethanol (1:1). Finally, the 3$\beta$-hydroxysterols are precipitated with an excess of digitonin, the precipitate is washed in acetone, dried under nitrogen, and dissolved in toluene:methanol (1:1). The $^3$H-labelled sterols are quantified by liquid scintillation and corrected for counting efficiency. In some tests 14C-cholesterol was added to initial extractions as an index of recovery, which averaged 80±3%

To measure inhibition of cholesterol synthesis, duplicate or triplicate aliquots of freshly isolated cells were suspended (100 mg cell net weight in 2.0 mL) in Eagle's Minimal Essential Medium containing bicarbonate and HEPES buffer, pH 7.35, plus 2% bovine serum albumin under a 95% $O_2$+5% $CO_2$ atmosphere. Cells were preincubated for 10 minutes with or without aliquots of test compounds added as water solutions of sodium salts or as dimethylsulfoxide solutions of lactones. Controls received vehicle alone. [$^3$H]-water (1.0 mCi per mL incubation volume) or 2-$^{14}$C-acetate (0.5 $\mu$Ci per mL incubation volume) was then added to each and the cells were incubated with constant shaking for 60 minutes at 37°. These conditions produced time-linear incorporation of tritium or $^{14}$C into sterols. The IC$_{50}$ for inhibition of sterol synthesis by test compounds which is shown in Table 2 was calculated from the linear regression curve of % inhibition (compared to controls) vs. log concentration using at least 4 concentrations of inhibitor. Test B therefore measures the ability of test substances to inhibit the intracellular synthesis of cholesterol.

TABLE 2

| Inhibition of Isolated Hepatocyte Cholesterol Biosynthesis | |
|---|---|
| Compound of Example No. | IC$_{50}$ nmolar |
| 8 | 27 |
| Mevinolin (Lovastatin) | 46.0 ± 26 |

The results of the above Tests A and B demonstrate that the compounds of Formula I inhibit cholesterol biosynthesis and, therefore, are useful in the treatment of hypercholesterolemia.

In another embodiment, this invention includes pharmaceutical compositions comprising at least one compound of Formula I in combination with a pharmaceutical carrier or diluent.

In another embodiment, this invention relates to a method of inhibiting cholesterol biosynthesis in an animal in need thereof, which comprises administering to said animal an effective cholesterol inhibitory dose of at least one compound of Formula I.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized.

Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active component, that is, the compound of Formula I according to the invention.

The compounds of Formula I may also be co-administered with pharmaceutically acceptable non-toxic cationic polymers capable of binding bile acids in a non-reabsorbable form in the gastrointestinal tract, e.g., cholestyramine, colestipol and poly [methyl-(3-trimethyl-aminopropyl)iminotrimethylene dihalide]. The relative amounts of polymer to compounds of this invention is between about 10:1 to about 10,000:1.

The dosage of the compounds of Formula I will depend not only on such factors as the weight of the patient and mode of administration, but also on the degree of cholesterol biosynthesis inhibition desired and the potency of the particular compound being utilized. The decision as to the particular dosage to be employed (and the number of times to be administered per day) is within the discretion of the physician, and may be varied by titration of the dosage to the particular circumstances of this invention for the satisfactory inhibition or reduction of cholesterol biosynthesis, each oral dosage unit will contain the active ingredient in an amount of from about 0.01 mg/kg to about 10 mg/kg body weight, and most preferably from about 0.05 mg/kg to about 2 mg/kg body weight. The active ingredient will preferably be administered in equal doses from one to four times a day. However, usually a small dosage is administered, and the dosage is gradually increased until the optimal dosage for the host under treatment is determined.

DESCRIPTION OF SPECIFIC EMBODIMENTS

In the following examples, all temperatures are given in degrees Centigrade. Melting points were recorded on a Thomas Hoover Melting Point Apparatus and are uncorrected. Proton magnetic resonance ($^1$H NMR) spectra were recorded on a Bruker AM 300, Burker WM 360, or Varian Gemini 300 Spectrometer. All spectra were determined in CDCl$_3$, DMSO-d$_6$ or D$_2$O unless otherwise indicated and chemical shifts are reported in δ units downfield from the internal standard tetramethylsilane (TMS) and interproton coupling constants are reported in Hertz (Hz). Splitting patterns are designated as follows: s, singlet; d, doublet, t, triplet; q, quartet; m, multiplet; br, broad peak; dd, doublet of doublet; dt, doublet of triplet; and dq, doublet of quartet.

Mass spectra were recorded on a Kratos MS-25 instrument utilizing the fast atom bombardment (FAB) technique or on a Finnigan 4500 instrument utilizing the EI or CI technique. The mass data are expressed in the format: parent ion (M+).

Analytical thin-layer chromatography (TLC) was carried out on precoated silica gel plates (60F-254) and visualized using UV light and/or iodine vapors. Column chromatography, also referred to as flash column chromatography, was performed in a glass column using finely divided silica gel (32–63 μm on silica gel-H) and pressures somewhat above atmospheric pressure with the indicated solvents. All evaporations of solvents were performed under reduced pressure. As used herein, the term hexanes is a mixture of isomeric C$_6$ hydrocarbons as specified by the American Chemical Society, and the term "inert" atmosphere is an argon or nitrogen atmosphere unless otherwise indicated.

EXAMPLE 1

Ethyl 3,3-bis(4-fluorophenyl)-3-hydroxy-2-(1-methylethyl)-propionate

Lithium diisopropylamide (22.2mL of 1.8M solution, 40 mmol) was added to a solution of ethyl isovalerate (5.2g, 40 mmol) in 40 mL of tetrahydrofuran at −40° C. After stirring for 0.5 hours and cooling to −70° C., 4,4'-difluorobenzophenone (4.36 g, 20 mmol) was added and the mixture stirred for 3 hours during which time the temperature was allowed to warm to −20° C. The reaction was quenched with 1N hydrochloric acid and the mixture extracted with diethyl ether. The extracts were dried with magnesium sulfate and concentrated in vacuo. The residue was crystallized from hexane to give 5.3 g of the title product; m.p. =118°-120° C.

Anal. Calcd. for C$_{20}$H$_{22}$F$_2$O$_3$: C, 68.96; H, 6.37.
Found : C, 69.02; H, 6.43.

EXAMPLE 2

Ethyl 3,3-bis(4-fluorophenyl)-2-(1-methylethyl)propenoate

A mixture of ethyl 3,3-bis(4-fluorophenyl)-3-hydroxy-2-(1-methylethyl)propionate (0.35 g, 1 mmol) and p-toluene sulfonic acid (0.1 g) in 20 mL toluene was heated at reflux for 1.5 hours. The mixture was concentrated in vacuo and the residue dissolved in diethyl ether. The ether solution was washed with saturated sodium bicarbonate solution, dried with magnesium sulfate and concentrated in vacuo. The residue was crystallized from cold petroleum ether to give 0.15 g of the title compound; m.p. =51.5°-52.5° C.

Anal. Calcd. for C$_{20}$H$_{20}$F$_2$O$_2$: C, 72.72; H, 6.11.
Found : C, 72.87; H, 6.11.

EXAMPLE 3

3,3-bis(4-fluorophenyl)-2-(1-methylethyl)propenol

Diisobutylaluminum hydride (118 mL of 1M solution in dichloromethane, 118 mmol) was added to a solution of ethyl 3,3-bis(4-flurorophenyl)-2-(1-methylethyl)-propenoate in 100 mL of dichloromethane at −75° C. After stirring for 30 minutes, analytical TLC (5% ethyl acetate in hexane on silica) indicated complete reduction. The reaction was quenched with 2N hydrochloric acid. The organic layer was separated, dried with magnesium sulfate and concentrated in vacuo. The solid residue was recrystallized from hexane to give 8.2 g of the title compound; m.p. =66°-68° C.

Anal. Calcd. for C$_{18}$H$_{18}$F$_2$O: C, 74.89; H, 6.30.
Found : C, 75.28; H, 6.46.

EXAMPLE 4

3,3-bis(4-fluorophenYl)-2-(1-methylethyl)propenal

A solution of 3,3-bis(4-fluorophenyl)-2-(1-methylethyl)-propenol (2.0 g, 6.9 mmol) and pyridinium chlorochromate (3 g) in 100 mL dichloromethane was stirred for 20 hrs. during which time a dark gummy solid separated. The solvent was decanted from the solid and concentrated in vacuo. The residue was extracted with hexane and the hexane solution concentrated in vacuo.

The residue was crystallized from petroleum ether to give 1.4 g of the title compound; m.p. =78°-84° C.

Anal. Calcd. for $C_{18}H_{16}F_2O$: C, 75.51; H, 5.64.
Found : C, 75.65; H, 5.67.

EXAMPLE 5

5,5-bis(4-fluorophenyl)-4-(1-methylethyl)-2,4-pentadienal

Lithium diisopropylamide (9 mL of 1.8M solution, 15 mmol) was added to N-ethylidenecyclohexanamine (7.5 mL of 2M solution, 15 mmol) in tetrahydrofuran at −40° C. After stirring for 30 minutes and cooling to −70° C., 3,3-bis(4-fluorophenyl)-2-(1-methylethyl)-propenal (1.43 g, 5.0 mmol) was added. The reaction was stirred −70° for 1.5 hrs. and quenched with 2N hydrochloric acid. The mixture was extracted with diethyl ether and the extracts concentrated in vacuo. The residue was stirred for 64 hours with a mixture of 50 mL of benzene, 35 mL acetic acid and 15 mL of water. The layers were separated and the aqueous layer extracted with diethyl ether. The combined organic solution was washed with saturated sodium bicarbonate solution, water, dried over magnesium sulfate and concentrated in vacuo. The residue was purified by silica gel chromatography eluting with 1% ethyl acetate in hexane and the material obtained crystallized from hexane to give 0.55 g of the title compound as a yellow solid; m.p. =105°-107° C.

Anal. Calcd. for $C_{20}H_{18}F_2O$: C, 76.91; H, 5.81.
Found : C, 77.18; H, 5.88.

EXAMPLE 6

1,1-Dimethylethyl 9,9-bis(4-fluorophenyl)-5-hydroxy-8-(1-methylethyl)-3-oxo-6,8-nonadienoate To a solution of 5,5-bis(4-fluorophenyl)-4-(1-methylethyl)-2,4-pentadienal (0.5 g, 1.6 mmol) in 20 mL tetrahydrafuran at −70° C., was added the dianion of t-butyl acetoacetate (2.1 mL of 1M solution in THF, 2.1 mmol) which was prepared by adding t-butyl acetoacetate (4.0 g, 25 mmol) in 4 mL tetrahydrofuran to a suspension of sodium hydride (1.0 g of 50% in oil, 25 mmol) in 6 mL tetrahydrofuran at −10° C., butyl lithium (11.4 mL of 2.2M solution) 25 mL was added and stirred for 0.5 hrs. After stirring for 2.5 hrs. the reaction was quenched with 2N hydrochloric acid. The mixture was extracted with diethyl ether. The extracts were dried over magnesium sulfate and concentrated in vacuo. The residue was purified by chromatography on silica gel eluting with 1% methanol in methylene chloride to give 0.5 g of the title compound as a clear oil. MS(CI): m/e =370 for M³;

Anal. Calcd. for $C_{28}H_{32}F_2O_4$: C, 71.47; H, 6.86
Found : C, 71.66; H, 7.14.

EXAMPLE 7

1,1-Dimethylethyl erythro-9,9-bis(4-fluorophenyl)-3,5-dihydroxy-8-(1-methylethyl)-6,8-nonadienoate Triethylborane (3.05 mL of 1M solution, 3.05 mmol) was added to a solution of 1,1-dimethylethyl 9,9-bis(4-fluorophenyl)-5-hydroxy-8-(1-methylethyl)-3-oxo-6,8-nonadienoate in tetrahydrofuran at -10° C. and the solution stirred for 1 hour. The solution was cooled to -78° C. and sodium borohydride (0.1 g) and 1.5 mL methanol were added. The mixture was stirred for 2 hrs. with cooling and diluted with 25 mL hexane and hydrolyzed with 2N hydrochloric acid. The organic layer was separated, washed successively with 1N hydrochloric acid, water and 1N sodium bicarbonate, dried with magnesium sulfate and concentrated in vacuo. The residue was purified by chromatography on silica gel to give the product as an oil which was crystallized from hexane to give 0.75g of the title compound; m.p. =75°-77° C. ¹H NMR (360 Hz) indicates only one diasteromer present.

Anal. Calcd. for $C_{28}H_{34}F_2O_4$: C, 71.17; H, 7.25
Found : C, 71.15; H, 7.30.

EXAMPLE 8

Erythro-9,9-bis(4-fluorophenyl)-3,5-dihydroxy-8-(1-methylethyl)-6,8-nonadienoic acid sodium salt A solution of 1,1-dimethylethyl erythro-9,9-bis(4-fluorophenyl)-3,5-dihydroxy-8-(1-methylethyl)-6,8-non-adienoate (1.25 g, 2.6 mmol) and sodium hydroxide (2.6 mL of 1N solution, 2.6 mmol) in 50 mL of ethanol was stirred for 3 hrs. and heated at reflux for 1.5 hours. The solution was concentrated in vacuo to give 1.05 g of the title compound as a powder; m.p. =245°-249° C. (dec).

Anal. Calcd. for $C_{24}H_{25}F_2O_4Na \cdot 0.25H_2O$: C, 65.08, H, 5.81
Found C, 64.82, H, 5.76.

EXAMPLE 9

Trans-6-[4,4-bis(4-fluorophenyl)-3-(1-methylethyl)-1,3-butadiethyl]-tetrahydro-4-hydroxy-2H-pyran-2-one A solution of erythro-9,9-bis(4-fluorophenyl)-3,5-dihydroxy-8-(1-methylethyl)-6,8-nonadienoic acid sodium salt (0.5 g, 1.1 mmol) in 10 mL of water was neutralized by adding 1N hydrochloric acid (1.1 mL, 1.1 mmol). The mixture was extracted with methylene chloride. The extracts were dried with magnesium sulfate and concentrated in vacuo. The residue was dissolved in toluene and the solution heated at reflux for 20 hours. The toluene was removed in vacuo. The residue was dissolved in methylene chloride and the solution concentrated in vacuo to give 0.38 g of the title compound as a powder; m.p. =45°-60° C.

Anal. Calcd. for $C_{24}H_{24}F_2O_3$, 72.35; H, 6.08
Found : C, 72.05; H, 6.14.

EXAMPLE 10

Ethyl 2-cyclohexyl-3,3-bis(4-fluorophenyl)-3-hydroxypropionate

Lithium diisopropylamide (56 mL of 1.8M, 100 mmol) was added to a solution of ethyl cyclohexylacetate (16.0 g, 100 mmol) in 50 mL tetrahydrofuran at −40° C. and the solution stirred for 0.5 hour. After further cooling to −70° C., 4,4'-difluorobenzophenone (10.9 g, 50 mmol) was added and the solution stirred for 1 hour at −70° C. and then allowed to warm to −10° C. during the next 2 hrs. The reaction was quenched with 2N hydrochloric acid and extracted with diethyl ether. The extracts were dried with magnesium sulfate and concentrated in vacuo. The residue was crystallized from hexane to give 158 g of the title compound; m.p. =118°-119° C.

Anal. Calcd. for $C_{23}H_{26}F_2O_3$: C, 71.12; H, 6.75
Found : C, 70.91; H, 6.75.

EXAMPLE 11

Ethyl 2-cyclohexyl-3,3-bis(4-fluorophenyl)propenoate

A mixture of ethyl 2-cyclohexyl-3,3-bis(4-fluorophenyl)-3-hydroxypropionate (15.0 g, 38.6 mmol) and p-toluenesulfonic acid (2.5 g) in 250 mL of toluene was heated at reflux for 2 hours. The mixture was cooled, washed with water and saturated sodium bicarbonate solution, dried over magnesium sulfate and concentrated in vacuo. The residue was crystallized from hexane to give 13.3 g of the title compound; m.p. =50°-55° C.

Anal. Calcd. for $C_{23}H_{24}F_2O_2$: C, 74.58; H, 6.54
Found : C, 74.66; H, 6.58.

EXAMPLE 12

2-Cyclohexyl-3,3-bis(4-fluorophenyl)propenol

Diisobutylaluminum hydride (148 mL of 1M solution, 148 mmol) was added to a solution of ethyl 2-cyclohexyl-3,3'bis(4-fluorophenyl)propenoate (13.3 g, 35.9 mmol) in 200 mL of dichloromethane at −70° C. After stirring for 2.5 hours the reaction was quenched with 2N hydrochloric acid. The organic layer was dried with magnesium sulfate and concentrated in vacuo. The residue was crystallized from hexane to give 10 g of the title compound; m.p. =96°-97° C.

Anal. Calcd. for $C_{21}H_{22}F_2O$: C, 76.81; H, 6.54
Found : C, 76.96; H, 6.84.

EXAMPLE 13

2-Cyclohexyl-3,3-bis(4-fluorophenyl)propenol

A solution of 2-cyclohexyl-3,3-bis(4-fluorophenyl)-propenol (10 g, 30.5 mmol) and pyridinium chlorochromate (15 g) in 100 mL of dichoromethane was stirred for 4 hours. The mixture was concentrated in vacuo and the residue extracted with hot hexane. The hexane extracts were concentrated in vacuo to give 8.9 g of the title compound as a pale yellow solid; m.p. =144°-146° C.

Anal. Calcd. for $C_{21}H_{20}F_2O$; C, 77.29, H, 6.18
Found : C, 77.22, H, 6.25.

EXAMPLE 14

4-Cyclohexyl-5,5-bis(4-fluorophenyl)-2,4-pentadienal

Lithium diisopropylamide (40 mL of 1.5M solution, 60 mmol) was added to a solution of N-ethylidenecyclohexanamine (30 mL of 2M solution, 60 mmol) in tetrahydrofuran at −10° C. After stirring for 30 minutes and further cooling to −50° C., 2-cyclohexyl-3,3-bis(4-fluorophenyl)propenal (8.4 g, 25.8 mmol) was added and the solution stirred for 3 hours during which time it was allowed to warm to 20° C. The solution was quenched with 2N hydrochloric acid and the mixture extracted with diethyl ether. The extracts were dried with magnesium sulfate and concentrated in vacuo. The residue was stirred for 4 days with a mixture of 100 mL benzene, 60 mL acetic acid and 40 mL water. The mixture was diluted with an additional 100 mL water and the layers separated. The organic phase was washed with water and saturated sodium bicarbonate solution, dried over magnesium sulfate and concentrated in vacuo. The residue was cyrstallized from hexane to give 6.0 g of the title compound; m.p. =116°-118° C.

Anal. Calcd. for $C_{23}H_{22}F_2O$; C, 78.39; H, 6.29
Found: C, 78.48; H, 6.45.

EXAMPLE 15

1,1-Dimethylethyl 8-cyclohexyl-9,9-bis(4-fluorophenyl)-5-hydroxy-3-oxo-6,8-nonadienoate The dianion of t-butyl acetoacetate (13 mL of 1M solution, 13 mmol; prepared as described in Example 6) was added to a solution of 4-cyclohexyl-5,5-bis(4-fluorophenyl)-2,4-pentadienal (3.75 g, 11 mmol) in tetrahydrofuran at −50° C. After stirring for 2.5 hours the solution was quenched with 2N hydrochloric acid and the mixture extracted with diethyl ether. The extracts were dried over magnesium sulfate and concentrated in vacuo. The residue was purified by chromatography on silica gel eluting with 0.5% methanol in methylene chloride to give 4.0 g of the title compound as an oil.

Anal. Calcd. for $C_{31}H_{36}F_2O_4$: C, 72.92; H, 7.11
Found: C, 70.22; H, 7.13

EXAMPLE 16

1,1-Dimethylethyl erythro-8-cyclohexyl-9,9-bis(4-fluorophenyl)-3,5-dihydroxy-6,8-nonadienoate Triethylborane (4.5 mL of 1M solution, 4.5 mmol) was added to a solution of 1,1-dimethylethyl 8-cyclohexyl-9,9-bis(4-fluorophenyl)-5-hydroxy-3-oxo-6,8-nonodienoate (2.0 g, 3.9 mmol) in tetrahydrofuran at −5° C. After stirring for 1 hour and further cooling to −70° C., sodium borohydride (0.23 g) and 2 mL of methanol were added. The mixture was stirred for 4 hours, diluted with 50 mL hexane and quenched with 1N hydrochloric acid. The mixture was extracted with diethyl ether. The extracts were dried over magnesium sulfate and concentrated in vacuo. The residue was dissolved in 50 mL methanol and the solution stirred for 72 hours. The solution was concentrated in vacuo and the residue purified by chromatography on silica gel eluting with 0.5% methanol in methylene chloride to give an oil. Crystallization from petroleum ether gave 0.76 g of the title compound; m.p. =83°-84° C. MS(EI): m/e =512 for M+.

Anal. Calcd. for $C_{31}H_{38}F_2O_4$: C, 72.64; H, 7.48
Found : C, 71.61; H, 7.41.

EXAMPLE 17

Erythro-8-cyclohexyl-9,9-bis(4-fluorophenyl)-3,5-dihydroxy-6,8-non-adienoic acid sodium salt A solution of 1,1-dimethylethyl erythro-8-cyclohexyl-9,9-bis(4-fluorophenyl)-3,5-dihydroxy-6,8-nonadienoate (0.65 g, 1.27 mmol) and sodium hydroxide (1.27 mmol) in 50 mL ethanol was stirred for 16 hours. The solution was concentrated in vacuo to give 0.55 g of the title compound as a beige powder; m.p. =150°-180° C.

Anal. Calcd. for $C_{27}H_{29}F_2O_4Na.H_2O$: C, 65.32; H, 6.30
Found : C, 65.12; H, 6.12.

EXAMPLE 18

Ethyl 3,3-bis(4-fluorophenyl)-3-hydroxy-2-methylpropionate

Butyl lithium (8.6 mL of 2.1M solution, 18 mmol) was added to a solution of N-isopropylcyclohexylamine (2.8 g, 20 mmol) in 20 mL tetrahydrofuran at −5° C. After stirring for 30 minutes and further cooling to −40° C., ethyl propionate (2.0 g, 20 mmol) was added and the solution stirred for 0.5 hr. After further cooling to −60° C., 4,4′-difluorobenzophenone (2.2 g, 10 mmol) was added and the solution stirred for 2 hours at −60 to −40° C. and for another 2 hours at −15° C. The reaction was quenched with 2N hydrochloric acid and the mixture extracted with diethyl ether. The extracts were dried with magnesium sulfate and concentrated in vacuo. The residue was crystallized from petroleum ether to give 1.95 g of the title compound as a white solid; m.p. =38°-40° C.

Anal. Calcd. for $C_{18}H_{18}F_2O_3$: C, 67.50; H, 5.67
Found: C, 67.20; H, 5.75.

EXAMPLE 19

Ethyl 3,3-bis(4-fluorophenyl)-2-methylpropenoate

A solution of ethyl 3,3-bis(4-fluorophenyl)-3-hydroxy-2-methylpropionate (0.5 g, 1.6 mmol) and p-toluenesulfonic acid (0.18 g) in toluene was heated at reflux for 2.5 hours. The solution was cooled and washed with saturated sodium bicarbonate solution and water. The organic layer was dried with magnesium sulfate and concentrated in vacuo. The residue was purified by chromatography on silica eluting with 0.5% ethyl acetate in hexane to give 0.2 g of the product as a clear oil which was crystallized from petroleum ether to give 0.15 g of the title compound; m.p. =75°-76° C.

Anal. Calcd. for $C_{18}H_{16}F_2O_2$: C, 71.51; H, 5.34
Found: C, 71.70; H, 5.46.

EXAMPLE 20

3,3-bis(4-fluorophenyl)-2-methylpropenol

Diisobutylaluminum hydride (80 mL of 1M solution, 80 mmol) was added to a solution of ethyl 3,3-bis(4-fluorophenyl)-2-methylpropenoate (8.0 g, 26.5 mmol) in 75 mL dichloromethane at −70° C. After stirring for 4 hours the solution was quenched with 1N hydrochloride acid. The organic layer was separated, dried with magnesium sulfate and concentrated in vacuo to give 5.5 g of the title compound as a clear oil. MS(EI): m/e =260 for M+ of $C_{16}H_{14}F_2O$.

EXAMPLE 21

3,3-bis(4-fluorophenyl)-2-methylpropenal

A solution of 3,3-bis(4-fluorophenyl)-2-methylpropenol (5.5 g, 21 mmol) and pyridinium chlorochromate (5.5 g) in 150 mL dichloromethane was stirred for 16 hours. The mixture was concentrated in vacuo and the dark residue extracted with several 50 mL volumes of hexane. The hexane solution was chromatographed on silica gel eluting with 2% ethyl acetate in hexane to give 2.0 g of the title compound; m.p. =77°-80° C.

Anal. Calcd. for $C_{16}H_{12}F_2O$: C, 74.42; H, 4.69
Foun:' C, 74.47; H, 4.59.

EXAMPLE 22

5,5-bis(4-fluorophenyl)-4-methyl-2,4-pentadienal

Lithium diisopropylamide (13 mL of 1.84M solution, 24 mmol) was added to N-ethylidenecyclohexanamine (12 mL of 2M solution, 24 mmol) in tetrahydrofuran at −40° C. After stirring for 30 minutes 3,3-bis(4-fluorophenyl)-2-methylpropenal (2.1 g, 8.1 mmol) was added and the solution stirred for 4 hours during which time the temperature was allowed to rise to −15° C. The solution was quenched with 2N hydrochloric acid and the mixture extracted with diethyl ether. The extracts were dried with magnesium sulfate and concentrated in vacuo. The residue was stirred for 16 hours with a mixture of 100 mL benzene, 65 mL acetic acid and 35 mL of water. The mixture was diluted to 500 mL with water and the aqueous layer was separated and extracted with diethyl ether. The combined organic solution was washed with saturated sodium bicarbonate and water, dried over magnesium sulfate and concentrated in vacuo. The residue was purified by chromatography on silica eluting with 1% ethyl acetate in hexane to give after hexane crystallization 1.5 g of the title compound; m.p. =86°-88° C.

Anal. Calcd. for $C_{18}H_{14}F_2O$: C, 76.05; H, 4.97
Found: C, 76.03; H, 4.74.

EXAMPLE 23

Methyl erythro-9,9-bis(4-fluorophenyl)-5-hydroxy-8-methyl-3-oxo-6,8-nonodienoate To a solution of 5,5-bis(4-fluorophenyl)-4-methyl-2,4-pentadienal (1.4 g, 2.9 mmol), in tetrahydrofuran at −50° C. was added the dianion of methyl acetoacetate (11.8 mL of 0.5M solution, 5.9 mmol; prepared as described for the t-butyl ester in Example 6). After stirring for 3 hours the reaction was quenched with 2N hydrochloric acid. The mixture was extracted with diethyl ether. The extracts were dried with magnesium sulfate and concentrated in vacuo. The residue was purified by chromatography on silica eluting with 1% methanol in methylene chloride to give 0.7 g of the title compound as an oil. MS(EI): m/e =400 for M+ of $C_{23}H_{22}F_2O_4$.

EXAMPLE 24

Erythro-9,9-bis(4-fluorophenyl)-3,5-dihydroxy-8-methyl-6,8nonadienoic acid sodium salt A. Methyl erythro-9-9-bis(4-fluorophenyl)-3,5-dihydroxy-8-methyl-6,8-nonadianoate Triethylborane (1.5 mL of 1M solution, 5.5 mmol) was added to a solution of methyl 9,9-bis(4-fluorophenyl)-5-hydroxy-8-methyl-3-oxo-6,8-nonadienoate in tetrahydrofuran at −50° C. After stirring at −5° C. for 1 hour, the solution was further cooled to −70° C. and sodium borohydride (0.1 g) and 1 mL of methanol were added. The reaction was stirred for 4 hours at −70° C. and hydrolyzed with 2N hydrochloric acid. The mixture was extracted with diethyl ether. The extracts were dried over magnesium sulfate and concentrated in vacuo. The residue was dissolved in methanol and the solution stirred for 18 hours. The solution was concentrated in vacuo and the residue purified by chromatography on silica eluting with 2% methanol in methylene chloride to give 0.38 g of the title compound as an oil.

B. Erythro-9,9-bis(4-fluorophenyl)-3,5-dihydroxy-8-methyl-6,8-nonadienoic acid sodium salt A solution of methyl erythro-9,9-bis(4-fluorophenyl)-3,5-dihydroxy-8-methyl-6,8-nonadienoate (0.38 g, 0.95 mmol) [prepared in Step A] and sodium hydroxide (0.95 mL of 1N solution, 0.95 mmol) in ethanol was stirred for 16 hours. The solution was concentrated in vacuo to give the title compound as a powder; m.p. =105°-120° C.

Anal. Calcd. for $C_{22}H_{21}F_2O_4 \cdot 2H_2O$: C, 59.20; H, 5.65
Found: C, 59.21; H, 5.04.

EXAMPLE 25

Ethyl 3-hydroxy-4-methyl-3-(1-methylethyl)pentanoate

Butyl lithium (167 mL of 2.1M solution, 350 mmol) was added to a solution of N-isopropylcyclohexylamine (49.5 g, 350 mmol) in 100 mL tetrahydrofuran at −5° C. After stirring for 30 minutes and cooling to −60° C., 2,4-dimethyl-3-pentanone (28.5 g, 250 mmol) was added and the solution stirred for 3 hours during which time the temperature was allowed to rise to −5° C. The reaction was quenched with 2N hydrochloric acid and the mixture extracted with diethyl ether. The extracts were dried with magnesium sulfate and the solution concentrated in vacuo. The residue was distilled at 100°–104° C. and 5 mm of Hg to give 37 g of the title compound as a liquid.

Anal. Calcd. for $C_{11}H_{22}O_3$: C, 65.32; H, 10.79
Found: C, 64.50; H, 10.91.

EXAMPLE 26

Ethyl 4-methyl-3-(1-methylethyl)pentanoate

A. Ethyl 4-methyl-3-(1-methylethyl)-2-pentenoate and ethyl 4-methyl-3-(1-methylethyl)-3-pentenoate Phosphorous oxychloride (32.9 g 220 mmol) was added to a solution of ethyl 3-hydroxy-4-methyl-3-(1-methylethyl)-pentanoate (22.0 g, 109 mmol) in 90 mL of pyridine at 0° C. The solution was stirred at 25° C for 18 hours and at 100° C. for 1.5 hours. After cooling and pouring over ice, the mixture was extracted with diethyl ether. The extracts were washed with 2N hydrochloric acid, dried with magnesium sulfate and concentrated in vacuo to give 20 g of the isomeric title compounds.

B. Ethyl 4-methyl-3-(1-methylethyl)pentanoate

The isomer mixture from Step A was dissolved in 75 mL of acetic acid and the solution reduced on the Parr apparatus with 1 g of platinium oxide for 72 hours. The catalyst was removed by filtration and the acetic acid removed in vacuo. The residue was dissolved in diethyl ether and the solution washed with saturated sodium bicarbonate solution, dried over magnesium sulfate and concentrated in vacuo. The residue was distilled under reduced pressure to give 13 g of the title compound; b.p. 87°–90° C./5 mm of Hg.

Anal. Calcd. for $C_{11}H_{22}O_2$: C, 70.93; H, 11.91
Found : C, 70.57; H, 11.76.

EXAMPLE 27

Ethyl 3,3-bis(4-fluorophenyl)-3-hydroxy-2-[2-methyl-1-(1methylethyl)propyl]propionate Butyl lithium (30.7 mL of 2.1M solution, 64.5 mmol) was added to a solution of N-isopropylcyclohexylamine(9.1 g, 64.5 mmol) in 50 mL of tetrahydrofuran at 5° C. After stirring for 30 minutes, the solution was cooled to −25° C. and ethyl 4-methyl-3-(1-methylethyl)pentanoate(12.0 g, 64.5 mmol) was added. After stirring for 30 minutes and further cooling to −70° C., 4,4′-difluorobenzophenone (17.1 g, 80 mmol) was added and the mixture stirred for 5 hours during which time the temperature was permitted to rise to −5° C. The mixture was quenched with 2N hydrochloric acid and extracted with diethyl ether. The extracts were dried and concentrated in vacuo. The residue was triturated with hexane to give 5 g of recovered 4,4′-difluorobenzophenone. The filtrate was concentrated in vacuo and the residue purified by chromatography on silica eluting with 0.5% ethyl acetate in hexane to give an oil. Crystallization with petroleum ether gave 1.2 g of the title compound; m.p. =69°–73° C.

Anal Calcd. for $C_{24}H_{30}F_2O_3$: C, 71.27; H, 7.48
Found : C, 70.38; H, 7.45.

EXAMPLE 28

Ethyl 3,3-bis(4-fluorophenyl)-2-[2-methyl-1-(1-methylethyl)-propyl]propenoate

Ethyl 3,3-bis(4-fluorophenyl)-3-hydroxy-2-[2-methyl-1(1-methylethyl)]propionate (0.5 g, 1.2 mmol) and p-toluenesulfonic acid (0.05 g) were added to 50 mL of refluxing toluene. After stirring for 1 hour at reflux, the mixture was cooled and washed with saturated sodium bicarbonate solution. The organic phase was dried and concentrated in vacuo to give 0.45 g of the title compound as a light yellow oil. MS(CI): m/e =386 for M+ of $C_{24}H_{28}F_2O_2$.

EXAMPLE 29

3,3-Bis(4-fluorophenyl)-2-[2-methyl-1-(1-methylethyl)-propyl]-propenol

Diisobutylaluminum hydride (33 mL of 1M solution, 33 mmol) was added to a solution of ethyl 3,3-bis(4-fluorophenyl)-2-[2-methyl-1-(1-methylethyl)-propyl]-propenoate (2.5 g, 6.5 mmole) in methylene chloride at −70° C. After stirring for 5 hours, the temperature had risen to −20° C. and the reaction was quenched with 2N hydrochloric acid. The organic layer was separated, dried with magnesium sulfate and concentrated in vacuo to give 2.1 g of the title compound as an oil. MS(CI): m/e =344 for M+ of $C_{22}H_{26}F_2O$.

EXAMPLE 30

3,3-Bis(4-fluorophenyl)-2-[2-methyl-1-(1-methylethyl)-propyl]propenal

Pyridinium chlorochromate (3.5 g) was added to a solution of 3,3-bis(4-fluorophenyl)-2-[2-methyl-1-(1-methylethyl)propyl]propenol (2.1 g, 6.1 mmol) in 75 mL of methylene chloride and the mixture stirred for 48 hours. The methylene chloride was decanted from the gummy precipitate which was washed with fresh solvent. The combined methylene chloride solutions were concentrated in vacuo to give a dark oil. The oil was triturated with 4×50 mL volumes of hexane. The hexane solutions were concentrated in vacuo to give 2.0 g of the title compound as a light yellow oil. M.S.(EI): m/e =342 for M+ of $C_{22}H_{24}F_2O$.

EXAMPLE 31

5,5-Bis(4-fluorophenyl-4-[2-methyl-1-(1-methylethyl)-propyl]-2,4-pentadienal

Lithium diisopropylamide (22 mL of 1.8M solution, 40 mmol) was added to a solution of N-ethylidenecyclohexanamine (20 mL of 2.0M solution, 40 mmole) in tetrahydrofuran at −30° C. After stirring for 30 minutes and cooling to −60° C., 3,3-bis(4-fluorophenyl)-2-[2-methyl-1-(methylethyl)propyl]propenal (4.5 g, 13.2 mmol) was added and the solution stirred for 4 hours during which time it was allowed to warm to −20° C. The reaction was quenched with water and the mixture extracted with diethyl ether. The extracts were dried with magnesium sulfate and concentrated in vacuo. The residue was stirred for 16 hours with a mixture of 100 mL of benzene, 60 mL of acetic acid and 40 mL of water. The mixture was diluted with 100 mL of water. The organic layer was separated, washed with water and saturated sodium bicarbonate, dried over magnesium sulfate and concentrated in vacuo to give 4.1 g of

EXAMPLE 32

1,1-Dimethylethyl 9,9-bis(4-fluorophenyl)-5-hydroxy-8-[2-methyl-1-(1-methylethyl)propyl]-3-oxo-6,8-nonadienoate A solution of the dianion of 1,1-dimethylethyl acetoacetate (15 mL of 1M solution, 15 mmol) was added to a solution of 5,5-bis(4-fluorophenyl)-4-[2-methyl-1-(1-methylethyl)propyl]-2,4-pentadienal (4.1 g, 11.1 mmol) in tetrahydrofuran at −60° C. After stirring for 3 hours the reaction was quenched with 2N hydrochloric acid and the mixture extracted with diethyl ether. The extracts were dried with magnesium sulfate and concentrated in vacuo. The residue was purified by chromatography on silica eluting with 5% ethyl acetate in hexane to give 3.2 g of the title compound as an oil. MS(CI): m/e =526 for M+ of $C_{32}H_{40}F_2O_4$.

EXAMPLE 33

1,1-Dimethylethyl erythro-9,9-bis(4-fluorophenyl)-3,5-dihydroxy-8-[2-methyl-1-(1-methylethyl)propyl]-6,8-nonadienoate Triethylborane (6.1 mL of 1M solution, 6.1 mL) was added to a solution of 1,1-dimethylethyl 9,9-bis-(4-fluorophenyl)-5-hydroxy-8-[2-methyl-1-(methylethyl)-propyl]-3-oxo-6,8-nonadienoate in tetrahydrofuran at −5° C., After stirring for 1 hour and further cooling to −70° C., sodium borohydride (0.75 g, 18 mmole) and 4 mL of methanol were added. The mixture was stirred for 3 hours, diluted with hexane and quenched with 2N hydrochloric acid. The mixture was extracted with diethyl ether. The extracts were dried and concentrated in vacuo. The residue was purified by chromatography on silica eluting with 5% ethyl acetate in hexane to give 1.5 g of the title compound as an oil.

EXAMPLE 34

Erythro-9,9-bis(4-fluorophenyl)-3,5-dihydroxy-8-[2-methyl-1-(1methylethyl)propyl]-6,8-nonadienoic acid sodium salt A solution of erythro-1,1-dimethylethyl 9,9-bis(4-fluorophenyl)-3,5-dihydroxy-8-[2-methyl-1-(1-methylethyl)propyl]-6,8-nonadienoate (0.95 g, 1,8 mmol) and sodium hydroxide (1.8 mL of 1N solution, 1.8 mmol) in ethanol was stirred for 16 hours at room temperature and heated for 8 hours at 75° C. The solution was concentrated in vacuo to give 0.5 g of the title compound as a powder; m.p. =80°-95° C.

Anal. Calcd. for $C_{28}H_{33}F_2O_4Na1.25H_2O$: C, 65.04; H, 6.92

Found : C, 64.89; H, 7.02.

EXAMPLE 35

Ethyl 3,3-bis(4-fluorophenyl)-3-hydroxy-2-(1,1-dimethylethyl)-propionate

Lithium diisopropylamide (21.7 mL of 1.8M solution, 40 mmol) was added to a solution of ethyl 3,3-dimethylbutyrate (5.76 g, 40 mmol) in 40 mL of tetrahydrofuran at −35° C. After stirring for 30 minutes and further cooling to −50° C., 4,4'-difluorobenzophenone (4.36 g, 2 mmol) was added. The reaction was stirred for 2 hours at −50° and for 2 hours at −20° C. The mixture was quenched with 2N hydrochloric acid and extracted with diethyl ether. The extracts were dried and concentrated in vacuo. The residue was crystallized from petroleum ether to give 4.55 g of the title compound; m.p. =93°-96° C.

Anal. Calcd. for $C_{21}H_{24}F_2O_3$: C, 69.60; H, 6.68

Found: C, 69.63, H, 6.48.

EXAMPLE 36

Ethyl 3,3-bis(4-fluorophenyl)-2-(1,1-dimethylethyl)propenoate

A mixture of ethyl 3,3-bis(4-fluorophenyl)-3-hydroxy-2-(1,1-dimethylethyl)propionate (1.0 g, 2.8 mmol) and p-toluenesulfonic acid (0.3 g) in 20 mL toluene was heated at reflux for 45 minutes. The mixture was cooled and concentrated in vacuo. The residue was purified by chromatography on silica eluting with 1% ethyl acetate in hexane. Concentration of the appropriate fractions gave an oil which was crystallized from petroleum ether to give 0.35 g of the title compound; m.p. =60°-62° C.

Anal. Calc'd for $C_{21}H_{22}F_2O_2$: C, 73.24; H, 6.44

Found : C, 73.20; H, 6.15.

EXAMPLE 37

3,3-Bis(4-fluorophenyl)-2-(1,1-dimethylethyl)propanol

Diisobutylaluminum hydride (20 mL of 1M solution, 20 mmol) was added to a solution of ethyl 3,3-bis(4-fluorophenyl)-2-(1,1dimethylethyl)propionate (2.0 g, 5.8 mmol) in 20 mL of methylene chloride at −70° C. The solution was stirred at −70° C. for 4 hours and at −10° C. for 18 hours. The solution was hydrolyzed by addition of 2N hydrochloric acid. The aqueous layer was separated and extracted with methylene chloride. The combined organic portions were dried with magnesium sulfate and concentrated in vacuo. The residue was crystallized from hexane to give 1.3 g of the title compound; m.p. =106°-108° C.

Anal. Calcd. for $C_{19}H_{20}F_2O$: C, 75.48; H, 6.67

Found: C, 75.43; H, 6.73.

EXAMPLE 38

3,3-Bis(4-fluorophenyl)-2-(1,1-dimethylethyl)propenal

A mixture of pyridinium chlorochromate (3.8 g) and 3,3-bis-(4-fluorophenyl)-2-(1,1-dimethylethyl)propanol (2.4 g, 7.9 mmol) in 100 mL of methylene chloride was stirred at 25° C. for 64 hours during which time a gummy precipitate separated. The solvent was decanted from the precipitate and the residue rinsed with two 50 mL portions of methylene chloride. The combined methylene chloride solution was concentrated in vacuo. The residue was triturated with three 60 mL portions of hexane. The hexane solution was concentrated in vacuo and the residue crystallized from fresh hexane to give 1.0 g of the title compound; m.p. =49°-51° C. MS(CI): m/e =300 for M+.

Anal. Calcd. for $C_{19}H_{18}F_2O$: C, 75.9 H, 6.05

Found : C, 74.81; H, 5.55.

EXAMPLE 39

5,5-Bis(4-fluorophenyl)-4-(1,1-dimethylethyl)-2,4-pentadienal

Lithium diisopropylamide (5.4 mL of 1.84M solution, 10 mmol) was added to N-ethylidenecyclohexanamine (5 mL of 2M solution, 10 mmol) in tetrahydrofuran at −20° C. After stirring for 30 minutes and further cooling to −50° C., 3,3-bis(4-fluorophenyl)-2-(1,1-dimethylethyl)propenal (0.9 g, 3.0 mmol) was added and the solution stirred for 4 hours during which time the temperature was allowed to rise to −20° C. The solution was quenched with 2N hydrochloric acid and the mixture extracted with diethyl ether. The extracts were dried and concentrated in vacuo. The residue was stirred for 18 hours with a mixture of 50 mL benzene, 15 mL of water and 35 mL of acetic acid. The mixture was diluted to 200 mL with water. The organic layer was separated, washed with saturated sodium bicarbonate solution, dried over magnesium sulfate and concentrated in vacuo. The residue was purified by chromatography on silica eluting with 1% ethyl acetate in hexane to give 0.5 g of the title compound; m.p. =87°–89° C.

Anal. Calcd. for $C_{21}H_{20}F_2O$: C, 77.29; H, 6.18
Found : C, 77.44; H, 6.16.

EXAMPLE 40

1,1-Dimethylethyl 9,9-bis(4-fluorophenyl)-5-hydroxy-8-(1,1-dimethylethyl)-oxo-6,8-nonadienoate The dianion of 1,1-dimethylethyl acetoacetate (9.1 mL of 1M solution, 9.1 mmol) was added to a solution of 5,5-bis-(4-fluorophenyl)-4-(1,1-dimethylethyl)-2,4-pentadienal in 30 mL of tetrahydrofuran at −60° C. The solution was quenched with 2N hydrochloric acid and the mixture extracted with diethyl ether. The extracts were dried and concentrated in vacuo. The residue was purified by chromatography on silica eluting with 0.5% methanol in methylene chloride to give 1.3 g of the title compound; m.p. =95°–97° C.

Anal. Calcd. for $C_{29}H_{34}F_2O_4$: C, 71.89; H, 7.08
Found : C, 71.66; H, 7.10.

EXAMPLE 41

1,1-Dimethylethyl erythro-9,9-bis(4-fluorophenyl)3,5-dihydroxy-8(1,1-dimethylethyl)-6,8-nonadienoate Triethylborane(2.5 mL of 1.0M solution, 2.5 mmol) was added to a solution of 1,1-dimethylethyl.9,9-bis(4-fluorophenyl)-5-hydroxy-8-(1,1-dimethylethyl)-3-oxo-6,8-nonadienoate (1.2 g, 25 mmol) in 30 mL of tetrahydrofuran at −10° C. After stirring for 1 hour the solution was cooled further to −60° C. and sodium borohydride (0.3 g, 7.5 mmol) and 2 mL of methanol were added. The mixture was stirred for 3 hours and hydrolyzed by addition of 2N hydrochloric acid. The mixture was extracted with methylene chloride. The extracts were dried with magnesium sulfate and concentrated in vacuo. The residue was dissolved in 50 mL of methanol and the solution stirred at room temperature for 16 hours. The methanol was removed in vacuo and the residue was purified by chromatography on silica eluting with 1% methanol in methylene chloride to give 1.0 g of the title compound; m.p. =96°–98° C.

Anal. Calcd. for $C_{29}H_{36}F_2O_4$: C, 71.59; H, 7.46
Found: C, 71.53; H, 7.48.

EXAMPLE 42

Erythro-9,9-bis(4-fluorophenyl)-3,5-dihydroxy-8-(1,1-dimethylethyl)-6,8-nonadienoic acid sodium salt A solution of 1,1-dimethylethyl erythro-9,9-bis(4-fluorophenyl)-3,5-dihydroxy-8-(1,1-dimethyethyl)-6,8-nonadienoate (0.5 g, 1.0 mmol) and sodium hydroxide (1.0 mL of 1.0N solution, 1.0 mmol) in 20 mL of ethanol was stirred for 16 hours. The solution was concentrated in vacuo to give 0.45 g of the title compound as a powder; m.p. =240°–244° C.

Anal. Calcd. for $C_{25}H_{27}F_2O_4Na\ H_2O$: C, 63.83; H, 6.22
Found: C, 63.53; H, 6.32.

EXAMPLE 43

Butyl cyclopropaneacetate

Thionyl chloride (10.7 g, 90 mmol) was added to cyclopropaneacetic acid (9.0 g 90 mmol) [*J. Med. Chem.* 27, 1291 (1984); *Chem. Lett.*, 1273 (1983); *J. Org. Chem.* 43. 3496 (1978)]. After stirring for 64 hours the liquid was dissolved in ether and added to a solution of butanol (6.7 g, 90 mmol) and triethylamine (9.1 g, 90 mmol) in 100 mL of diethyl ether at 0° C. The mixture was stirred for 16 hours and washed with water. The organic phase was dried over magnesium sulfate and concentrated in vacuo. The residue was distilled at 46° C. at 2 mm of Hg to give 7 g of the title compound. MS(CI): m/e =156 for M+ of $C_9H_{16}O_2$.

EXAMPLE 44

Butyl 2-cyclopropyl-3,3-bis(4-fluorophenyl)-3-hydroxypropionate

Butyl lithium (5 mL of 2M solution, 10 mmol) was added to a solution of N-isopropylcyclohexylamine(1.4 g, 10 mmol) in 20 mL of tetrahydrofuran at −10° C. After stirring for 30 minutes and cooling to −70° C., butyl cyclopropaneacetate (1.5 g 10 mmol) was added. After stirring for an additional 30 minutes, 4,4'-difluorobenzophenone (1.1 g, 5 mmol) was added and the mixture stirred for 6 hours at −70° C. The mixture was quenched with 2N hydrochloric acid and extracted with diethyl ether. The extracts were dried and concentrated in vacuo. The residue was purified by chromatography on silica eluting with 0.75% ethyl acetate in hexane to give 1.0 g of the title compound; m.p. =77°–80° C.

Anal. Calcd. for $C_{22}H_{24}F_2O_3$: C, 70.58; H, 6.47
Found: C, 70.43; H, 6.32.

EXAMPLE 45

Butyl 2-cyclopropyl-3,3-bis(4-fluorophenyl)propenoate

Phosphorous oxychloride (1 mL) was added slowly to a solution of butyl 2-cyclopropyl-3,3-bis(4-fluorophenyl)-3-hydroxypropionate (0.2 g, 0.53 mmol) in 4.5 mL of pyridine at −10° C. After stirring for 18 hours at 25° C., the mixture was heated at 100°–110° C. for 1.25 hours. The mixture was poured over ice and extracted with diethyl ether. The extracts were dried with magnesium sulfate to give 0.15 g of the title compound as an oil. MS(FAB): m/e =356 for M+ of $C_{22}H_{22}F_2O_2$.

EXAMPLE 46

2-Cyclopropyl-3,3-bis(4-fluorophenyl)-2-propenol

Diisobutylaluminum hydride (6.6 mL of 1M solution, 6.6 mmol) was added to a solution of butyl 2-cyclohexyl-3,3-bis(4-fluorophenyl)propenoate (0.8 g, 2.2 mmol) in 10 mL of methylene chloride at −70° C. After stirring for 2.0 hours the mixture was hydrolyzed by adding 2N hydrochloric acid. The organic layer was separated, washed with water, dried over magnesium sulfate and concentrated in vacuo. The residue was crystallized from hexane to give 0.4 g of the title compound; m.p. =88°-90° C.

Anal. Calcd. for $C_{18}H_{16}F_2O$: C, 75.51; H, 5.64
Found : C, 75.20; H, 5.31.

EXAMPLE 47

2-Cyclopropyl-3,3-bis(4-fluorophenyl)-2-propenal

A solution of 2-cyclopropyl-3,3-bis(4-fluorophenyl)-2-propenol (0.3 g, 1.0 mmol) and pyridinium chlorochromate (0.5 g) in 20 mL of methylene chloride was stirred at 25° C for 18 hours during which time a gummy solid formed. The methylene chloride was decanted from the solid and the solution concentrated in vacuo. The residue was stirred with diethyl ether; the diethyl ether was decanted from some insoluble tar and the diethyl ether concentrated in vacuo. The residue was crystallized from petroleum ether to give 0.1 g of the title compound; m.p. =86°-88° C.

Anal. Calcd. for $C_{18}H_{14}F_2O$: C, 76.05; H, 4.97
Found: C, 75.85; H, 4.94.

EXAMPLE 48

4-Cyclopropyl-5,5-bis(4-fluorophenyl)-2,4-pentadienal

Butyl lithium (2.9 mL of 1M solution, 6 mmol) was added to a solution of N-isopropylcyclohexylamine (0.85 g, 6 mmol) in 10 mL of tetrahydrofuran at −20° C. After stirring for 30 minutes and further cooling to −50° C., N-ethylidenecyclohexanamine (3 mL of 2M solution, 6 mmol) was added. After stirring for an additional 30 minutes and continued cooling to −70° C., 2-cyclopropyl-3,3-bis(4-fluorophenyl)-2-propenal (0.85 g, 2 mmol) was added. The mixture was stirred for 4 hours at −70° C. and quenched with saturated ammonium chloride. The mixture was extracted with diethyl ether. The diethyl ether was dried with magnesium sulfate and concentrated in vacuo. The residue was stirred for 16 hours with a mixture of 50 mL of benzene, 15 mL of acetic acid and 35 mL of water. The mixture was diluted to 250 mL with water and extracted with diethyl ether. The extracts were washed with saturated sodium bicarbonate solution, dried over magnesium sulfate and concentrated in vacuo. The residue was crystallized from hexane to give 0.38 g of the title compound; m.p. =139°-140° C.

Anal. Calcd. for $C_{20}H_{16}F_2O$: C, 77.41; H, 5.20
Found: C, 77.26; H, 5.35.

EXAMPLE 49

1,1-Dimethylethyl 8-cyclopropyl-9,9-bis(4-fluorophenyl)-5-hydroxy-3-oxo-6,8-nonadienoate The dianion of 1,1-dimethylethyl acetoacetate (22 mL of 0.5M solution, 11 mmol) was added to a solution of 4-cyclopropyl-5,5-bis(4-fluorophenyl)-2,4-pentadienal (2.0 g, 9.7 mmol) in 30 mL tetrahydrofuran at −70° C. The mixture was stirred for 2.5 hours at −70° C. and quenched with saturated ammonium chloride solution. The mixture was extracted with diethyl ether; the extracts were dried over magnesium sulfate and concentrated in vacuo to give 3,0 g of the title compound as an oil. MS(CI): m/e =468 for M+ of $C_{28}H_{30}F_2O_4$.

EXAMPLE 50

1,1-Dimethylethyl erythro-8-cyclopropyl-9,9-bis(4-fluorophenyl)-3,5-dihydroxy-6,8-nonadienoate Triethylborane (4 mL of 1M solution, 4 mmol) was added to a solution of 1,1-dimethylethyl 8-cyclopropyl-9,9-bis(4-fluorophenyl)-5-hydroxy-3-oxo-6,8-nonadienoate (1.0 g, 2.1 mmol) in 20 mL tetrahydrofuran at 0° C. After stirring for 30 minutes and further cooling to −70° C., sodium borohydride (0.1 g, 2.5 mmol) and 1.5 mL of methanol were added. After stirring for 2.0 hours, the mixture was diluted with 50 mL of hexane and quenched with water. Solid carbon dioxide was added and the mixture was stirred until evolution of gas ceased. The mixture was extracted with diethyl ether. The extracts were dried over magnesium sulfate and concentrated in vacuo. The residue was dissolved in methanol and the solution allowed to stir for 16 hours. The methanol was removed in vacuo and the residue purified by chromatography on silica eluting with 10% ethyl acetate in hexane to give 0.7 g of the title compound as a clear oil. MS(EI): m/e =470 for M+ of $C_{28}H_{32}F_2O_4$.

EXAMPLE 51

Erythro-8-cyclopropyl-9,9-bis(4-fluorophenyl)-3,5-dihydroxy-6,8-nonadienoic acid sodium salt A solution of 1,1-dimethylethyl erythro-8-cyclopropyl-9,9-bis(4-fluorophenyl)-3,5-dihydroxy-6,8-nonodienoate (0.7 g, 1.5 mmol) and sodium hydroxide (1.5 mL of 1N solution) was stirred for 16 hours at 25° C. and concentrated in vacuo to give 0.55 g of the title compound; m.p. =168°-170° C.

Anal. Calcd. for $C_{24}H_{23}F_2O_4$ Na $H_2O$: C, 63.44; H, 5.55
Found: C, 63.84; H, 5.52.

EXAMPLE 52

Ethyl 2-ethyl-3,3-bis(4-fluorophenyl)-3-hydroxypropionate

Butyl lithium (65.7 mL of 2.1M solution, 138 mmol) was added to a solution of N-isopropylcyclohexylamine in 100 mL tetrahydrofuran at −20° C. After stirring for 1 hour and cooling to −40° C., ethyl butyrate (16.0 g, 138 mmol) was added. After stiring for an additional hour and further cooling to −70° C., 4,4'-difluorobenzophenone (15 g, 68.8 mmol) was added. The solution was stirred for 3 hours at −70° C., allowed to warm to 20° C. during the next 5 hours and stirred at 20° C. for 8 hours. The reaction was quenched with 2N hydrochloric acid and the mixture extracted with diethyl ether. The extracts were dried and concentrated in vacuo. The residue was crystallized from hexane to give 11.7 g of the title compound; m.p. =99°-101° C.

Anal. Calcd. for $C_{19}H_{20}F_2O_3$: C, 68.26; H, 6.03
Found: C, 68.35; H, 6.06.

EXAMPLE 53

Ethyl 2-ethyl-3,3-bis(4-fluorophenyl)propenoate

A mixture of ethyl 2-ethyl-3,3-bis(4-fluorophenyl)-3-hydroxypropionate (1.0 g, 3.0 mmol) and p-toluenesulfonic acid (0.2 g) in 100 mL toluene was heated at reflux for 1.25 hours. The mixture was cooled and washed with saturated sodium bicarbonate solution and water. The solution was dried with magnesium sulfate and concentrated in vacuo. The residue was crystallized from petroleum ether to give 0.85 g of the title compound; m.p. =57°-59° C.

Anal. Calcd. for $C_{19}H_{18}F_2O_2$: C, 72.14; H, 5.74
Found: C, 72.25; H, 5.82.

EXAMPLE 54

2-Ethyl-3,3-bis(4-fluorophenyl)-2-propenol

Diisobutylaluminum hydride (79 mL of 1M solution, 79 mmol) was added to a solution of ethyl 2-ethyl-3,3-bis(4-fluorophenyl)propenoate (8.3 g, 26.3 mmol) in 150 mL of methylene chloride at −70° C. After stirring for 3 hours, the mixture was hydrolyzed by adding 2N hydrochloric acid. The aqueous fraction was separated and extracted with methylene chloride. The combined organic fractions were dried with magnesium sulfate and concentrated in vacuo to give 7 g of the title compound as an oil; MS(CI): m/e =274 for $M^+$ of $C_{17}H_{16}F_2O$.

EXAMPLE 55

2-Ethyl-3,3-bis(4-fluorophenyl)-2-propenal

Activated manganese dioxide (49 g) was added to a solution of 2-ethyl-3,3-bis(4-fluorophenyl)-2-propenol (7 g, 25.5 mmol) in 100 mL of methylene chloride and the mixture stirred for 18 hours. The insolubles were removed and the solution concentrated in vacuo to give 6.9 g of the title compound as an oil. MS(CI): m/e =272 for $M^+$ of $C_{17}H_{14}F_2O$.

EXAMPLE 56

4-Ethyl-5,5-bis(4-fluorophenyl)-2,4-pentadienal

Butyl lithium (25.7 mL of 2.1M solution, 54 mmol) was added to a solution of N-isopropylcyclohexylamine in 30 mL tetrahydrofuran at −10° C. After stirring for 30 minutes and cooling to −40° C., N-ethylidenecyclohexamine (27 mL of 2M solution, 54 mmol) was added and the solution stirred for 30 minutes. The solution was further cooled to −70° C. and 2-ethyl-3,3-bis(4-fluorophenyl)- 2-propenal(4.9 g, 18 mmol) in 40 mL of tetrahydrofuran was added. The mixture was stirred for 5 hours and quenched with water. The mixture was extracted with diethyl ether, the extracts dried over magnesium sulfate and concentrated in vacuo. The residue was stirred with a mixture of 100 mL of benzene, 40 mL of water and 60 mL of acetic acid for 16 hours and diluted with 1.50 mL of water. The organic layer was separated, washed with saturated sodium bicarbonate solution, dried with magnesium sulfate and concentrated in vacuo. The residue was crystallized from petroleum ether to give 3.45 g of the title compound; m.p. =98°-99.5° C.

Anal. Calcd. for $C_{19}H_{16}f_2O$: C, 76.50; H, 5.41
Found: C, 76.32; H, 5.72.

EXAMPLE 57

1,1-Dimethylethyl 8-ethyl-9,9-bis(4-fluorophenyl)-5-hydroxy-3-oxo-6,8-nondienoate)

The dianion of 1,1-dimethylethyl acetoacetate (20 mL of 0.5 M solution, 10 mmol) was added to a solution of 4-ethyl- 5,5-bis-(4-fluorophenyl)-2,4-pentadienal (2.0 g, 6.7 mmol) in 20 mL of tetrahydrofuran at −70° C. The mixture was stirred for 3 hours during which time the temperature was allowed to rise to −30° C. and quenched with saturated ammonium chloride solution. The mixture was extracted with diethyl ether, the extracts dried over magnesium sulfate and concentrated in vacuo. The residue was purified by chromatography on silica eluting with 10% ethyl acetate in hexane to give 2.2 g of the title compound as an oil. MS(CI): m/e =456 for $M^+$ of $C_{27}H_{30}F_2O_4$.

EXAMPLE 58

1,1-Dimethylethyl erythro-8-ethyl-9,9-bis(4-fluorophenyl)-3,5-dihydroxy-6,8-nonadienoate Triethylborane (4.8 mL of 1M solution, 4.8 mmol) was added to a solution of 1,1-dimethyethyl 8-ethyl-9,9-bis(4-fluorophenyl)-5-hydroxy-3-oxo-6,8-nonadienoate (2.2 g, 4.8 mmol) in 25 mL tetrahydrofuran at 0° C. After stirring for 30 minutes, the solution was cooled to −70° C. and sodium borohydride (0.4 g, 10 mmol) and 2 mL of methanol were added. The mixture was stirred for 3 hours and quenched with saturated ammonium chloride. Several pieces of solid carbon dioxide were added and the mixture stirred until gas evolution ceased. The mixture was extracted with diethyl ether; the extracts were dried over magnesium sulfate and concentrated in vacuo. The residue was dissolved in 50 mL of methanol and the solution stirred for 16 hours. The methanol was removed in vacuo and the residue crystallized from hexane to give 1.8 g of the title compound; m.p. =90°-91° C.

Anal. Calcd. for $C_{27}H_{32}F_2O_4$: C, 70.73; H, 7.04
Found: C, 71.19; H, 7.15.

EXAMPLE 59

Erythro-8-ethyl-9,9-bis(4-fluorophenyl)-3,5-dihydroxy-6,8-non adienoate sodium salt A solution of 1,1-dimethylethyl erythro-8-ethyl-9,9-bis(4-fluorophenyl)-3,5-dihydroxy-6,8-nonadienoate (0.82 g, 1.8 mmol) and sodium hydroxide (1.8 mL, 1.8 mmol) in 20 mL of ethanol was stirred for 16 hours. The solution was concentrated in vacuo to give 0.8 g of the title compound; [m.p. =247°-250° C. (dec).

Anal. Calcd. for $C_{23}H_{23}F_2O_4Na.0.5H_2O$: C, 63.74; H, 5.59
Found: C, 63.77; H, 5.54.

EXAMPLE 60

3,3-Difluoro-1,1-bis(4-fluorophenyl)-2-methylpropene

A solution of 3,3-bis(4-fluorophenyl)-2-methylpropenal (0.52 g, 2 mmol) [prepared in Example 21] and diethylaminosulfur trifluoride (0.64 g, 8 mmol) was stirred for 64 hours. The solution was added to water and the mixture was extracted with diethyl ether. The extracts were dried with magnesium sulfate and concentrated in vacuo. The residue was purified by chromatography on silica eluting with hexane to give 0.25 g of the title compound as an oil. MS(CI): m/e =280 for $M^+$ of $C_{16}H_{12}F_4$.

EXAMPLE 61

2-Bromomethyl-3,3-difluoro-1,1-bis(4-fluorophenyl)-2-methuylpropene

A mixture of 3,3-difluoro-1,1-bis(4-fluorophenyl)-2-methylpropene (1.1 g, 3.9 mmol), N-bromosuccinimide (0.71 g, 4.0 mmol) and a trace of azaisobutyric dinitrile in 100 mL of carbon tetrachloride was stirred at reflux for 6 hours and at room temperature for 64 hrs. The mixture was concentrated in vacuo and the residue purified by chromatography on silica eluting with hexane to give 0.7 g of the title compound as an oil. MS(CI): m/e =358 for M+ of $C_{16}H_{11}BrF_4$.

EXAMPLE 62

Dimethyl [3,3-bis(4-fluorophenyl)-2-difluoromethyl-2-propen-1-yl]phosphonate

A solution of 2-bromomethyl-3,3-difluoro-1,1-bis(4-fluorophenyl)propene (0.5 g, 1.4 mmol) and trimethylphosphite (0.5 g, 4 mmol) was heated at relfux for 20 minutes. Excess trimethyl phosphite was removed in vacuo and the residue purified by chromatography on silica eluting with 40% ethyl acetate to give 0.4 g of the title compound as a viscous oil. MS(EI): m/e =388 for M+ of $C_{18}H_{17}F_4O_3P$.

EXAMPLE 63

1,1-Dimethylethyl 2,2-dimethyl-6-(2-phenylethenyl)-1,3-dioxane-4-acetate

To a solution of 1,1-dimethylethyl 3,5-dihydroxy-7-phenyl-6-heptenoate (5.5 g, 19 mmol) in acetone (2.3 g, 40 mmol) was added a catalyic amount of p-toluenesulfonic acid. After stirring for 2 hours, the mixture had solidified and was dissolved in excess acetone and filtered through a pad of sodium carbonate. The excess acetone was removed in vacuo and the residue crystallized from isopropyl ether to give 3.4 g of the title compound; m.p. =91°-93° C.

Anal. Calcd. for $C_{20}H_{28}O_4$: C, 72.27; H, 8.50
Found: C, 71.98; H, 8.91.

EXAMPLE 64

1,1-Dimethylethyl 6-formyl-2,2-dimethyl-1,3-dioxane-4-acetate

Ozone was bubbled into a solution of 1,1-dimethylethyl 2,2-dimethyl-6-(2-phenylethenyl)-1,3-dioxane-4-acetate (3.0 g, 9 mmol) in 100 mL of methylene chloride at −78° C. until a blue color persisted. Nitrogen was then bubbled into the solution without cooling until the color disappeard. The temperature had risen to −20° C. Methyl sulfide (3 mL) was added and the solution stirred for 18 hours. The solvent was removed in vacuo and the residue purified by chromatography on silica eluting with 20% ethyl acetate in hexane to give 1.78 g of solid. Recrystallization from pentane gave the title compound as a white solid; m.p. =71°-73° C.

Anal. Calcd. for $C_{13}H_{22}O_5$: C, 60.45; H, 8.59
Found: C, 60.28; H, 8.64.

EXAMPLE 65

1,1-Dimethylethyl 6-[3-difluoromethyl-4,4-bis(4-fluorophenyl)-1,3-butadienyl]-1,3-dioxane-4-acetate Butyl lithium (1.04 mL of 2.5M solution, 2.6 mmol) was added to a solution of dimethyl [3,3-bis(4-fluorophenyl)-2-difluoromethyl-2-propen-1-yl]phosphonate (1.0 g, 2.6 mmol) in 10 mL of tetrahydrofuran at −78° C. After stirring for 30 minutes, 1,1-dimethylethyl 6-formyl-2,2-dimethyl-1,3-dioxane-4-acetate (0.82 g, 3.2 mmol) was added and the mixture stirred for 64 hrs. at room temperature. The mixture was quenched with saturated ammonium chloride solution and extracted with diethyl ether. The extracts were dried over magnesium sulfate and conentrated in vacuo. The residue was purified by chromatography on silica eluting with 5% ethyl acetate in hexane to give an oil. Crystallization from pentane gave 0.6 g of the title compound; m.p. =124°-125° C.

Anal. Calcd. for $C_{29}H_{32}F_4O_4$: C, 66.92; H, 6.20
Found: C, 66.41; H, 6.17.

EXAMPLE 66

1,1-Dimethylethyl erythro-8-difluoromethyl-9,9-bis(4-fluorophenyl)-3 5-dihydroxy-6,8-nonadienoate A suspension of 1,1-dimethylethyl 6-[3-difluoromethyl-4,4-bis(fluorophenyl)-1,3-butadienyl]-1,3-dioxane-4-acetate (0.6 g, 1.15 mmol) in methanol (10 mL) was acidified with p-toluenesulfonic acid. The solid gradually dissolved and after 30 minutes thin-layer chromatography (25% ethyl acetate in hexane on silica) indicated complete reaction. The solution was concentrated in vacuo, the residue dissolved in diethyl ether and the insolubles removed. The diethyl ether was concentrated in vacuo to give 0.55 g of the title compound as an oil. MS(CI): m/e =480 for M+ of $C_{26}H_{26}F_4O_4$.

EXAMPLE 67

Erythro-8-difluoromethyl-9,9-bis(4-fluorophenyl)-3,5-dihydroxy-6,8-nonadienoic acid sodium salt hydrate A solution of 1,1-dimethylethyl erythro-8-difluoromethyl-9,9-bis(4-fluorophenyl)-3,5-dihydroxy-6,8-nonadienoate (0.55 g, 1.1 mmol) and sodium hydroxide (1.1 mL of 1N solution, 1.1 mmol) were stirred for 16 hours. The solution was concentrated in vacuo to give the title compound as a beige powder; m.p. =75°-90° C.

Anal. Calcd. for $C_{22}H_{19}F_4O_4Na \cdot 0.75 H_2O$: C, 57.46; H, 4.50
Found: C, 57.68; H, 4.42.

EXAMPLE 68

3,3,3-Trifluoro-1,1-bis(4-fluorophenyl)-2-methylpropene

Lithium (1.94 g, 280 mmol) was added to a suspension of titanium trichloride (12.3 g, 80 mmol) in 250 mL tetrahydrofuran. After the initial exothermic reaction had subsided, the mixture was heated at reflux for 2 hours. After cooling to 25° C. a solution of 4,4'-difluorobenzophenone (2.18 g, 10 mmol) and 1,1,1-trifluoroacetone (4.48 g, 40 mmol) in 30 mL tetrahydrofuran was added and the mixture stirred for 2 hours. The mixture was then refluxed for 20 hours. The mixture was cooled and diluted with 30 mL of hexane and the insolubles removed by filtration through diatomaceous earth. The solution was concentrated in vacuo and the residue purified by chromatography on silica eluting with hexane to give 0.7 g of the title compound as an oil. MS(CI): m/e =298 for M+ of $C_{16}H_{11}F_5$.

EXAMPLE 69

2-Bromomethyl-3,3,3-trifluoro-1,1-bis(4-fluorophenyl)-propane

A mixture of N-bromosuccimimide (0.36 g, 2.0 mmol),3,3,3-trifluoro-1,1-bis(4-fluorophenyl)-2-methylpropene and azoisobutyric dinitrile (0.1 g) was heated at reflux for 48 hours. The insolubles were removed and the solution concentrated in vacuo. The residue was purified by chromatogrpahy on silica eluting with hexane to give 0.2 g of product as an oil. Crystallization from pentane gave the title compound; m.p. =60°-61° C.

Anal. Calcd. for $C_{16}H_{11}B_6F_5$: C, 50.96; H, 2.68
Found: C, 51.00; H, 2.76.

EXAMPLE 70

Dimethyl
3,3-bis(4-fluorophenyl)-2-trifluoromethyl-2-propen-1yl]
phosphonate

A solution of 2-bromomethyl-3,3,3-trifluoro-1,1-bis(4-fluorophenyl)propene (1.1 g, 2.9 mmol) and trimethyl phosphite (1.1 g, 9 mmol) was at reflux for 30 minutes. The excess trimethyl phosphite was removed in vacuo. The reside was purified by chromatography on silica gel eluting with 30% ethyl acetate in hexane to give 1.2 g of the title compound as an oil. MS(CI): m/e =406 for M+ of $C_{18}H_{16}F_5O_3P$.

EXAMPLE 71

1,1-Dimethylethyl
6-[4,4-bis(4-fluorophenyl)-3-trifluoromethyl-1,3-butadienyl]-1,3-dioxane-4-acetate Butyl lithium(1.2 mL of 2.5M solution, 3.0 mmol) was added to a solution of dimethyl [3,3-bis(4-fluorophenyl)-2-trifluoromethyl-2-propen-1-yl]phosphonate in 20 mL tetrahydrofuran at −70° C. followed by immediate addition of 1,1-dimethylethyl 6-formyl-2,2-dimethyl-1,3-dioxane-4-acetate (0.9 g, 3.6 mmol). The solution was allowed to gradually warm to room temperature and then stirred for 14 hours. The reaction was quenched with saturated ammonium chloride solution and the mixture extracted with diethyl ether. The extracts were dried and concentrated in vacuo. The residue was purified by chromatography on silica eluting with 10% ethyl acetate in hexane to give 0.7 g of the title compound as an oil. MS(CI): m/e =538 for M+ of $C_{29}H_{31}F_4O_4$.

EXAMPLE 72

1,1-Dimethylethyl
erythro-9,9-bis(4-fluorophenyl)-3,5-dihydroxy-8-trifluoromethyl-6,8-nonadienoate A solution of 1,1-dimethylethyl 6-[4,4-bis-(4-fluorophenyl)-3-trifluoromethyl-1,3-butadienyl]-1,3-dioxane-4-acetate (0.7 g, 1.3 mmol) in 10 mL of methanol was acidified with p-toluenesulfonic acid. After stirring for 2.5 hours the solution was concentrated in vacuo. The residue was dissolved in diethyl ether and filtered through sodium carbonate. The diethyl ether solution was concentrated in vacuo and the residue purified by chromatography on silica eluting with 20% ethyl acetate in hexane to give 0.5 g of the title compound as an oil. MS(CI): m/e =498 for M+ of $C_{26}H_{27}F_5O_4$.

EXAMPLE 73

Erythro9,9-bis(4-fluorophenyl)-3,5-dihydroxy-8-trifluoromethyl-6,8-nonadienoic acid sodium salt A solution of 1,1-dimethylethyl erythro-9,9-bis(4-fluorophenyl)-3,5-dihydroxy-8-trifluoromethyl-6,8-nonadienoate (10.4 g, 0.8 mmol) and sodium hydroxide (0.8 mL of 1N solution, 0.8 mmol) in 10 mL of ethanol was stirred for 20 hours. The solution was evaporated and the residue dissolved in methanol. The methanol was removed in vacuo to give 0.35 g of the title compound as a powder; m.p. =110°-140° C.

Anal. Calcd. for $C_{22}H_{18}f_5O_4Na.0.75\ H_2O$: C, 55.30; H, 4.12
Found: C, 55.34; H, 4.50.

EXAMPLE 74

2-Difluoromethyl-3,3-bis(4-fluorophenyl)propenal

2-Nitropropane (0.27 g, 3 mmol) was added to a solution of sodium ethoxide prepared by dissolving sodium (0.06 g, 2.8 mmol) in 50 mL ethanol. after stirring for 30 minutes, 2-bromomethyl-3,3-difluoro-1,1-bis(4-fluorophenyl)-2-methylpropene (0.7 g, 2.5 mmol) (prepared in example 61) was added and the mixture stirred for 18 hours. The mixture was diluted to 100 mL with water and stirred for 2 hours. The aqueous mixture was extracted with diethyl ether. The extracts were dried over magnesium sulfate and concentrated in vacuo. NMR of the crude indicated a mixture containing the title compound and 2-difluoromethyl-3,3-bis(4-fluorophenyl)-propenol. The crude mixture was dissolved in methylene chloride and stirred for 72 hours with activated manganese dioxide. The insoluble inorganic solid was removed by filtration and the filtrate concentrated in vacuo. The residue was purified by chromatography on silica eluting with 1% ethyl acetate in hexane to give 0.1 g of the title compound as an oil. MS(CI): m/e =294 for M+ of $C_{16}H_{10}F_4O$.

What is claimed is:

1. A compound of the formula

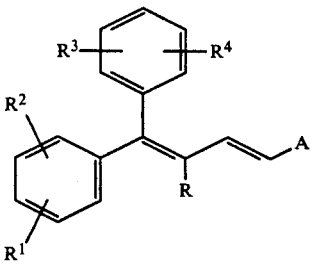

I wherein
$R^1$, $R^2$, $R^3$ and $R^4$ each are independently hydrogen, halogen, $C_{1-4}$ alkyl, $C_{1-4}$ alkoxy or trifluoromethyl;
R is $C_{1-7}$ alkyl, $C_{3-6}$ cycloalkyl, fluoromethyl, difluoromethyl or trifluoromethyl;
A is

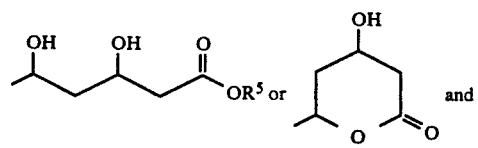

and $R^5$ is hydrogen, a hydrolyzable ester group or a cation to form a non-toxic pharmaceutically acceptable salt.

2. A compound of claim 1 wherein $R^1$, $R^2$, $R^3$ and $R^4$ each are independently hydrogen, fluoro, choro or methyl.

3. A compound of claim 2 wherein R is 1-methylethyl.

4. A compound of claim 2 wherein R is ethyl.

5. A compound of claim 2 wherein R is cyclopropyl.

6. A compound of claim 2 wherein R is 1,1-dimethylethyl.

7. A compound of claim 2 wherein R is trifluoromethyl.

8. The compound of claim 3 which is erythro-9,9-bis(4-fluorophenyl)-3,5-dihydroxy-8-(1-methylethyl)-6,8-nonadienoic acid or a non-toxic pharmaceutically acceptable salt.

9. The compound of claim 8 which is the (3R, 5S) enantiomer of 9,9-bis(4-fluorophenyl)-3,5-dihydroxy-8-(1-methylethyl)-6,8-nonadienoic acid or a non-toxic pharmaceutically acceptable salt.

10. The compound of claim 3 which is trans-6-[4,4-bis(4-fluorophenyl)-3-(1-methylethyl)-1,3-butadienyl]-tetrahydro-4-hydroxy-2H-pyran-2-one.

11. The compound of claim 10 which is the (4R,6S) enantiomer of 6-[4,4-bis(4-fluorophenyl)-3-(1-methylethyl)-1,3-butadienyl]-tetrahydro-4-hydroxy-2H-pyran-2-one.

12. The compound of claim 4 which is erythro-9,9-bis(4-fluorophenyl)-3,5-dihydroxy-8-ethyl-6,8-nonadienoic acid or a non-toxic pharmaceutically acceptable salt.

13. The compound of claim 5 which is erythro-9,9-bis(4-fluorophenyl)-3,5-dihydroxy-8-cyclopropyl-6,8-nonadienoic acid or a non-toxic pharmaceutically acceptable salt.

14. The compound of claim 6 which is erythro-9,9-bis(4-fluorophenyl-3,5-dihydroxy-8-(1,1-dimethylethyl)-6,8-nonadienoic acid or a non-toxic pharmaceutically acceptable salt.

* * * * *